United States Patent
Nishino et al.

[11] Patent Number: 6,017,937
[45] Date of Patent: Jan. 25, 2000

[54] PYRIDINE DERIVATIVE, ANTI-ULCER DRUG, AND ANTIBACTERIAL DRUG

[75] Inventors: Chikao Nishino; Fumitaka Sato, both of Yokohama; Tomohiro Uetake, Tokyo; Hirotada Fukunishi, Yokohama; Nao Kojima, Tokyo, all of Japan

[73] Assignee: Shiseido Co., Ltd., Tokyo, Japan

[21] Appl. No.: 09/055,921

[22] Filed: Apr. 7, 1998

[30] Foreign Application Priority Data

Mar. 18, 1996 [JP] Japan ..................................... 8-90625
Mar. 5, 1997 [JP] Japan ..................................... 9-69166

[51] Int. Cl.$^7$ ........................ A61K 31/44; C07D 213/75; C07D 213/81
[52] U.S. Cl. ........................ 514/345; 514/340; 514/352; 514/353; 546/292; 546/297; 546/298; 546/306
[58] Field of Search .................... 546/292, 297, 546/298, 306; 514/345, 346, 352, 353

[56] References Cited

U.S. PATENT DOCUMENTS

| | | | |
|---|---|---|---|
| 4,916,145 | 4/1990 | Tilley et al. | 514/357 |
| 5,340,827 | 8/1994 | Beeley et al. | 514/352 |
| 5,340,828 | 8/1994 | Graham et al. | 514/357 |

*Primary Examiner*—Alan L. Rotman
*Attorney, Agent, or Firm*—Snider & Chao, LLP; Fei-Fei Chao; Ronald R. Snider

[57] ABSTRACT

A pyridine derivative or a salt thereof expressed by the following formula 1:

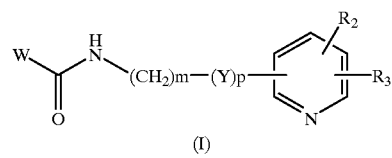

formula 1 wherein W represents a group expressed by the following formula 2 or formula 3;

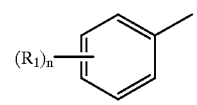

formula 2

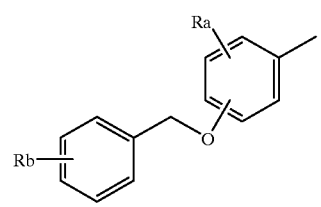
formula 3 wherein $R_1$ represents an alkenyloxy group;
n represents 1 or 2;
Ra represents a lower alkyl group; and
Rb represents a halogen atom; and wherein
each of $R_2$ and $R_3$ represents a hydrogen atom, a lower alkyl group, a lower alkoxy group, or halogenated alkyl group;
Y represents a group expressed by —S—, —NH— or —CONH—;
m represents an integer of 0 to 2; and
p represents 0 or 1.

The pyridine derivative has an anti-ulcer effect or an antibacterial activity against *Helicobacter pyroli* to be available for prevention or cure of ulcers.

17 Claims, 4 Drawing Sheets

Reaction formula A;

Reaction formula A;

Reaction formula B;

Reaction formula C;

Reaction formula D;

Reaction formula E;

Reaction formula F;

Reaction formula G;

Reaction formula H;

Reaction formula I;

Reaction formula J;

Reaction formula K;

Reaction formula L;

PYRIDINE DERIVATIVE, ANTI-ULCER DRUG, AND ANTIBACTERIAL DRUG

This is a divisional application of U.S. patent application No. 08/818,281 (filed on Mar. 17, 1997) now U.S. Pat. No. 5,859,032.

RELATED APPLICATIONS

This application claims the priority of Japanese Patent Application No.8-90625 filed on Mar. 18, 1996, and Japanese Patent Application which title is PYRIDINE DERIVATIVE, ANTI-ULCER DRUG, AND ANTIBACTERIAL DRUG and which inventors are Chikao Nishino, Fumitaka Sato, Tomohiro Uetake, Hirotada Fukunishi, and Nao Kojima filed on Mar. 5, 1997 by SHISEIDO CO., LTD. as applicant, which are incorporated herein by reference.

FIELD OF THE INVENTION

The present invention relates to a pyridine derivative and, in particular, to a pyridine derivative having an antibacterial activity against *Helicobacter pyroli* or an anti-ulcer effect.

BACKGROUND OF THE INVENTION

Various theories have been proposed with respect to a cause of ulcer in human. In particular, it has been elucidated that stress, taking of non-steroidal anti-inflammatory drugs for curing rheumatic diseases, and the like are closely related to ulcer formation, mainly due to relatively excess gastric acid secretion. Accordingly, it is important to suppress the acid secretion in order to prevent ulcer formation and to cure it.

On the other hand, it has been considered that *Helicobacter pyroli*, which is a rod normally existing in stomach, generates ammonia due to its strong urease activity, thereby inducing ulcer and persistence of itself. Since it persistently lives within mucus and mucosa, it becomes the greatest cause for recurrence of ulcer. Accordingly, it has been considered that the recurrence of ulcer can be prevented if this bacterium is sterilized.

Though various kinds of medicaments for curing ulcer have been conventionally developed, few medicaments have been known to have an effect for preventing stress ulcers from generating and an antibacterial activity against *Helicobacter pyroli*.

DISCLOSURE OF THE INVENTION

In view of the problems of the above-mentioned prior art, the object of the present invention is to provide a compound which is excellent in preventing ulcer from generating and to provide antibacterial drug against *Helicobacter pyroli* and anti-ulcer drug including such a compound as a main component.

As a result of the diligent studies conducted by the inventors, it has been found that a specific pyridine derivative is effective against various kinds of ulcer due to its antibacterial property against *Helicobacter pyroli* or its acid secretion inhibition as a main action mechanism. Thus, the present invention has been accomplished.

Namely, a pyridine derivative or a salt thereof in accordance with the present invention is expressed by the following formula 1:

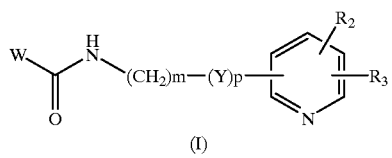

formula 1 wherein W represents a group expressed by the following formula 2 or formula 3;

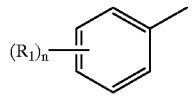

formula 2

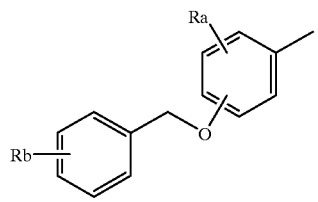

formula 3 wherein $R_1$ represents an alkenyloxy group;

n represents 1 or 2;

Ra represents a lower alkyl group; and

Rb represents a halogen atom; and wherein each of $R_2$ and $R_3$ represents a hydrogen atom, a lower alkyl group, a lower alkoxy group, or halogenated alkyl group;

Y represents a group expressed by —S—, —NH— or —CONH—;

m represents an integer of 0 to 2; and p represents 0 or 1.

An antibacterial drug against *Helicobacter pyroli* in accordance with the present invention comprises, as an effective ingredient, said pyridine derivative or the pharmacologically acceptable salt thereof, together with a pharmaceutically acceptable carrier and/or adjuvant.

An anti-ulcer drug in accordance with the present invention comprises, as an effective ingredient, said pyridine derivative or the pharmacologically acceptable salt thereof, together with a pharmaceutically acceptable carrier and/or adjuvant.

A method for the treatment of peptic ulcers in man or mammals in accordance with the present invention comprises administering an effective amount of said pyridine derivative or the pharmacologically acceptable salt thereof to a host.

A method for the inhibition of acid secretion in stomach of man or mammals in accordance with the present invention comprises administering an effective amount of said pyridine derivative or the pharmacologically acceptable salt thereof to a host.

A method for the inhibition of growth of *Helicobacter pyroli* in stomach of man or mammals in accordance with the present invention comprises administering an effective amount of said pyridine derivative or the pharmacologically acceptable salt thereof to a host.

A method for the prevention of peptic ulcers in man or mammals in accordance with the present invention comprises administering an effective amount of said pyridine derivative or the pharmacologically acceptable salt thereof to a host.

EXAMPLES

Figure 1:
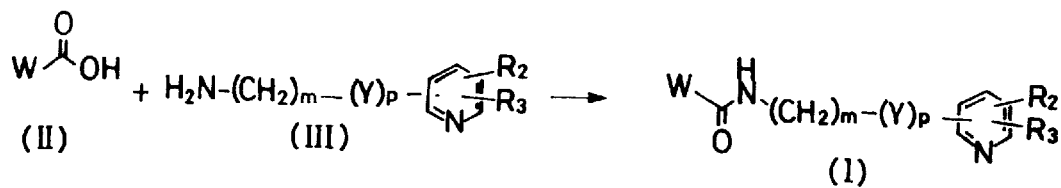
FIG. 1 shows an example of a step for manufacturing the pyridine derivative in accordance with the present invention and FIGS. 2 to 12 show examples of steps for manufacturing material compounds for the pyridine derivative in accordance with the present invention.

In the compound in accordance with the present invention, the alkenyl group of "alkenyloxy group" found at $R_1$ refers to a straight or branched alkenyl group which has at least one double bond and has 2 to 20 carbon atoms. An alkenyloxy group refers a group in which a hydrogen atom of a hydroxy group is substituted by such an alkenyl group. It is preferably a branched alkenyloxy group from the viewpoint of effect. Examples thereof include prenyloxy group, geranyloxy group, neryloxy group and farnesyloxy group. Preferably, it is prenyloxy or geranyloxy group. While the double bond has two kinds of configurations, namely, cis and trans, each double bond in alkenyloxy group may have either configurations.

In the present invention, n represents 1 or 2 and, when n is 1, it is preferable that $R_1$ is bonded to para-position to an amide group.

Each of $R_2$ and $R_3$, which may be identical to or different from each other, is hydrogen atom, a lower alkyl group, a lower alkoxy group or a halogenated alkyl group. A preferable example thereof is hydrogen atom.

The lower alkyl group found at $R_2$ and $R_3$ is a straight or branched alkyl group having 1 to 6 carbon atoms. Examples thereof include methyl, ethyl, n-propyl, n-butyl, isopropyl, isobutyl, 1-methylpropyl, tert-butyl, n-pentyl, 1-ethylpropyl, isoamyl, and n-hexyl group. Particularly preferably, they are methyl groups.

The lower alkoxy group found at $R_2$ and $R_3$ represents a group derived from the above-mentioned lower alkyl group. The particularly preferable example thereof is methoxy group.

The halogenated alkyl group found at $R_2$ and $R_3$ represents a group in which the above-mentioned lower alkyl group is halogenated. A specifically preferable example of such a lower alkyl group is methyl group. Examples of such a halogen atom include fluorine, chlorine, bromine, and iodine atom. In the halogenated alkyl group, more than one thereof can be bonded to above-mentioned alkyl group. Trifluoromethyl group is a preferable example of the halogenated alkyl group.

Y represents a group expressed by —S—, —NH—, or —CONH— and, preferably, —NH—.

The lower alkyl group found at Ra can be exemplified by the above-mentioned lower alkyl group. Preferably, it is a branched alkyl group and, more preferably, isobutyl group.

Examples of the halogen atom found at Rb include fluorine, chlorine, bromine, and iodine atom. The particularly preferable example thereof is fluorine atom.

A preferable compound of the present invention may be expressed by the following formula 4:

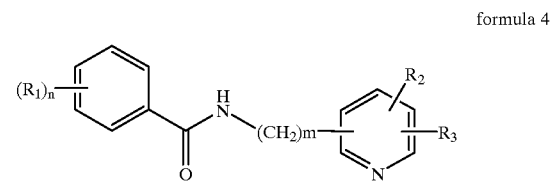

formula 4 wherein $R_1$, $R_2$, $R_3$, n, and m are same as those in the above-mentioned formula 1.

In formula 4, $R_2$ and $R_3$ are preferably hydrogen atoms.

In formula 1 or 4, it is preferable that n is 1 and R is bonded to para-position.

In formula 1 or 4, n is 2 preferably.

A preferable compound of the present invention may be expressed by the following formula 5:

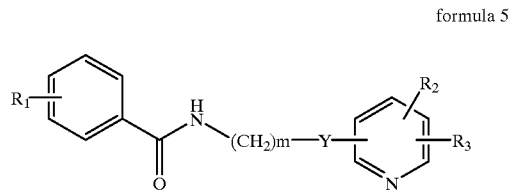

formula 5 wherein $R_1$, $R_2$, $R_3$, Y, and m are same as those in the above-mentioned formula 1.

In formula 5, Y is a group expressed by —NH— preferably.

In formula 5, $R_1$ is bonded to para-position preferably.

In a compound in accordance with the present invention, $R_1$ is prenylaxy group or geranyloxy group preferably.

A preferable compound of the present invention may be expressed by the following formula 6:

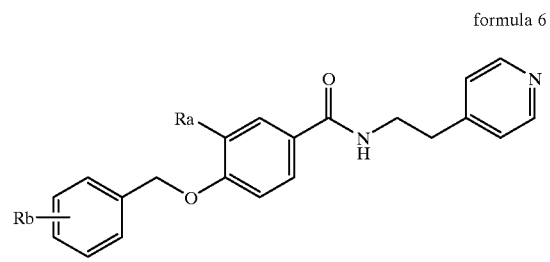

formula 6 wherein Ra and Rb are same as those in the above-mentioned formula 3.

In formula 6, it is preferably that Ra is isobutyl group and Rb is fluorine atom.

The pyridine derivatives and its pharmacologically acceptable salts in accordance with the present invention, have anti-ulcer effect, acid secretion inhibition effect, and anti-bacterial effect against *Helicobacter pyroli* as well as a high safety. Accordingly, they are effective as medicaments for preventing and curing various ulcer.

The compound of the present invention is a novel compound which has not been conventionally disclosed. As similar compounds, there have been known a pyridine derivative having a platelet activating factor antagonism in Japanese Unexamined Patent Publication No. 5-213877 (EP 530, 444) and U.S. Pat. No. 4,916,145, a pyridine derivative having a cardiac muscle protecting effect in U.S. Pat. No. 4,743,610, and a pyridine derivative having a phosphodiesterase IV inhibiting effect in U.S. Pat. No. 5,340,827.

However, all of them do not relate to the pharmacological effect of the present invention Also, the pyridine derivative in accordance with the present invention is characterized in that W in the basic skeleton of formula 1 is a phenyl group having one or two alkenyloxy groups as shown in formula 2 or a phenyl group having both of a benzyloxy group substituted by halogen and a lower alkyl group. Such a pyridine derivative has not been known even from the viewpoint of structure. Accordingly, the pyridine derivative of the present invention is a novel compound completely.

In the following, while the general method for manufacturing the compound of the present invention will be explained, it should not be restricted thereto.

The compound(I) of the present invention can be expressed by formula 1 can be manufactured by reaction formula A shown in FIG. 1.

In reaction formula A, the pyridine derivative(I) of the present invention can be obtained from a carboxylic acid(II) and a amine(III), by using a known amide-bond forming reaction such as mixed anhydride method, acid chloride method, DCC method, CDI method, or azide method. Here, W, $R_2$, $R_3$, m, p, and Y in reaction formula A are defined as formula 1 mentioned above.

In the mixed anhydride method, by using an activator such as diphenyl phosphinic chloride, ethyl chloroformate, isobutyl chloroformate, or pivaloyl chloride, the carboxylic acid (II) is converted into its corresponding anhydride and then reacted with the amine (III). As an additive, for example, an organic base such as triethyl amine, pyridine, or N-methylmorpholine is used. As a solvent, for example, a halogenated hydrocarbon such as dichloromethane or chloroform; an aromatic hydrocarbon such as benzene, toluene, or xylene; an ether such as tetrahydrofuran or dioxane; or an amide such as dimethylformamide or dimethylacetamide is used. While the reaction temperature and reaction time may be changed according to the material compounds used, the reaction is usually effected at a temperature within the range of $-15°$ C. to the reflux temperature of the solvent.

In the acid chloride method, as an activator, for example, phosphorus pentachloride, phosphorus trichloride, or thionyl chloride is used to convert the carboxylic acid (II) into the corresponding acid chloride and then the latter is reacted with the amine (III). As an additive, for example, an organic base such as triethyl amine, pyridine, or N-methylmorpholine is used. As a solvent, for example, a halogenated hydrocarbon such as dichloromethane or chloroform; an aromatic hydrocarbon such as benzene, toluene, or xylene; or an amide such as dimethyl formamide or dimethylacetamide is used. While the reaction temperature and reaction time may be changed according to the material compounds used, the reaction is usually effected at a temperature within the range of $0°$ C. to the reflux temperature of the solvent.

In the DCC method, as a condensing agent, for example, dicyclohexyl carbodiimide (DCC) or 1-ethyl-3-(3-dimethylaminopropyl)carbodiimide hydrochloride (WSCI) is used. As a solvent, for example, a halogenated hydrocarbon such as dichloromethane or chloroform; an aromatic hydrocarbon such as benzene, toluene, or xylene; an ether such as tetrahydroftran or dioxane; or an amide such as dimethylformamide or dimethylacetamide is used. If necessary, this reaction may be effected while 1-hydroxybenzotriazole (HOBt) or N-hydroxy succinimide (HOSu) is added thereto. While the reaction temperature and reaction time may be changed according to the material compounds used, the reaction is usually effected at a temperature within the range of $0°$ C. to the reflux temperature of the solvent.

In the CDI method, as an activator, for example, N,N'-carbonyldiimidazole is used to convert the carboxylic acid (II) into the corresponding N-acyl derivative and then the latter is reacted with the amine(III). As an additive, for example, an organic base such as triethyl amine, pyridine, or N-methylmorpholine or an inorganic base such as sodium hydride or potassium hydride is used. As a solvent, for example, a halogenated hydrocarbon such as dichloromethane or chloroform; an aromatic hydrocarbon such as benzene, toluene, or xylene; an ether such as tetrahydrofuran or dioxane; or an amide such as N,N-dimethylformamide or N,N-dimethylacetamide is used. While the reaction temperature and reaction time may be changed according to the material compounds used, the reaction is usually effected at a temperature within the range of $0°$ C. to the reflux temperature of the solvent.

In the azide method, as an activator, for example, diphenylphosphorylazide is used to convert the carboxylic acid (II) into the corresponding azide and then the latter is reacted with the amine (III). As an additive, for example, an organic base such as triethylamine, pyridine, or N-methylmorpholine is used. As a solvent, for example, a halogenated hydrocarbon such as dichloromethane or chloroform; an aromatic hydrocarbon such as benzene, toluene, or xylene; or an amide such as dimethylformamide or dimethylacetamide is used. While the reaction temperature and reaction time may be changed according to the material compounds used, the reaction is usually effected at a temperature within the range of $0°$ C. to the reflux temperature of the solvent.

Figure 2:
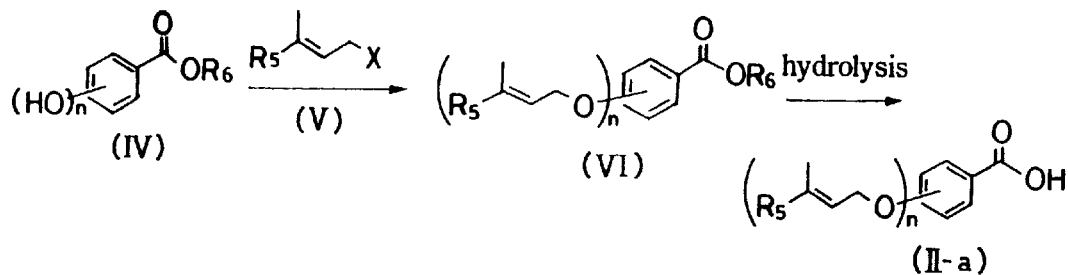
Figure 3:
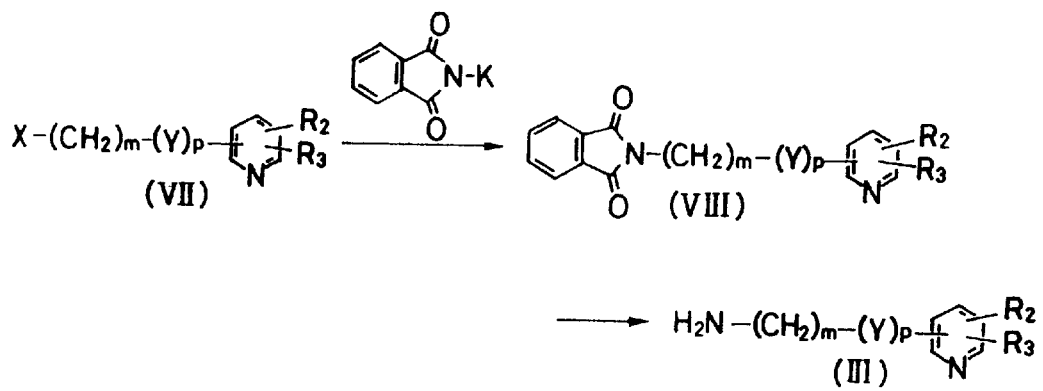

Specifically, for example, diphenylphosphinic chloride or pivaloyl chloride is used as an activator for the mixed anhydride method, while triethylamine is used as an additive to effect the reaction in a solvent such as chloroform or N,N-dimethyl formamide at a temperature within the range of $-15°$ C. to room temperature, thereby attaining the aimed object Among the carboxylic acids(II) which are material compounds in reaction formula A, the compound wherein W is a group expressed by formula 2 can be synthesized by reaction formula B shown in FIG. 2.

In reaction formula B, n represents an integer of 1 or 2. $R_6$ represents a carboxyl-protecting group which may be a lower alkyl group such as methyl group, ethyl group, or tert-butyl group, phenacyl group, or trichloroethyl group as long as no problem occurs in the subsequent reaction. X represents a halogen atom and $R_5$ represents methyl or prenyl group.

In reaction formula B, an alkenyl halide(V) is reacted with a hydroxy compound(IV) in the presence of a base and then hydrolyzed so as to synthesize the carboxylic acid (II-a).

The first step of this reaction can be effected in the presence of a base. Sodium amide, triethylamine, sodium hydride, sodium hydroxide, potassium carbonate, barium oxide, silver oxide, or the like is used therefor. Also, a catalytic amount of potassium iodide can be added thereto. As a solvent, for example, an alcohol such as methanol, ethanol, or butanol; an aromatic compound such as benzene, toluene, xylene, or pyridine; an ether such as diethylether, tetrahydrofuran, or dioxane; an amide such as dimethylformamide or dimethylacetamide; or a ketone such as dimethylsulfoxide or acetone is used. While the reaction temperature and reaction time may be changed according to the material compounds used, the reaction is usually effected at a temperature within the range of $0°$ C. to the reflux temperature of the solvent.

Specifically, for example, the compound (IV) is dissolved in tetrahydrofuran or N,N'-dimethylformarnide and, after sodium hydride as a base is added and stirred therein, the alkenyl halide(V) is added thereto so as to effect a reaction at a temperature within the range of room temperature to the reflux temperature of the solvent, thereby attaining the aimed object.

In the reaction of the second step, the ester compound (VI) is hydrolyzed in the presence of an acid or a base so as to synthesize the carboxylic acid (II-a). Hydrochloric acid, sulfuric acid, p-toluenesulfonic acid, or the like can be used as the acid, while sodium hydroxide, potassium hydroxide, potassium t-butoxide, or the like can be used as a base. As a solvent, a carboxylic acid such as formic acid or acetic acid, an alcohol such as methanol or ethanol; water; or a mixed solvent thereof can be used. While the reaction temperature and reaction time can be changed according to the material compounds used, the reaction is usually effected at a temperature within the range of 0° C. to the reflux temperature of the solvent.

Specifically, for example, the ester compound(VI) is dissolved in an alcohol such as methanol or ethanol and then an aqueous sodium hydroxide or potassium hydroxide solution is added thereto so as to effect a reaction at a temperature within the range of room temperature to reflux temperature, thereby attaining the aimed object.

The amine (III) which is a material compound in reaction formula A can be synthesized, for example, by reaction formulas C to G shown in FIGS. 3 to 7.

In the formula C, a halogenated compound(VII) is reacted with a phthalimide by using Gabriel's method and then hydrolyzed so as to synthesize the primary amine(III). Here, in reaction formula C, Y, $R_2$, $R_3$, m, and p are defined as those in formula 1, while X represents a halogen atom.

At the first step in reaction formula C, as a solvent, for example, an aromatic compound such as benzene, toluene, or xylene; an ether such as tetrahydrofuran or dioxane; or an amide such as dimethylformamide or dimethylacetamide is used. While the reaction temperature and reaction time may be changed according to the material compounds used, the reaction is usually effected at a temperature within the range of 0° C. to the reflux temperature of the solvent.

Specifically, for example, the halogenated compound (VII) is dissolved in dimethylformamide and potassium phthalimide is added thereto so as to effect a reaction at a temperature within the range of room temperature to the reflux temperature of the solvent, thereby attaining the aimed object.

At the second step in reaction formula C, hydrolysis by a conventionally used acid or base, or the reaction by hydrazine can be used. In the reaction by hydrazine, an alcohol, for example, such as methanol or ethanol can be used as a solvent,. While the reaction temperature and reaction time may be changed according to the material compounds used, the reaction is usually effected at a temperature within the range of 0° C. to the reflux temperature of the solvent.

Figure 4:
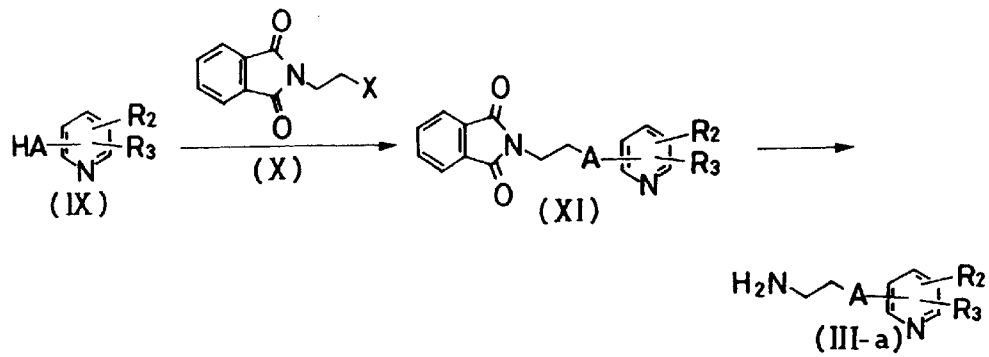
Figure 5:
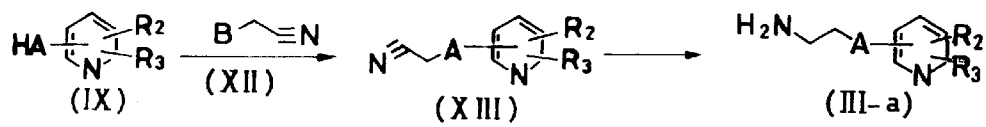

The compound (III-a) wherein Y is —S— or —NH—, p is 1, and m is 2 in the material compound(III) in reaction formula A can be obtained, for example, by reaction formulas D to E shown in FIGS. 4 to 5.

In reaction formula D, a halogenoethylphtalimide is reacted with a substituted pyridine compound (IX) and then the resulting compound is hydrolyzed, thereby synthesizing the amine (III-a). Here, in reaction formula D, A represents —S— or —NH—, while $R_2$ and $R_3$ are defined as those in formula 1. X represents a halogen atom.

At the first step of this reaction, the reaction can be effected in the presence of a base. Sodium amide, triethylamine, sodium hydride, sodium hydroxide, potassium carbonate, barium oxide, silver oxide, or the like is used therefor. Also, a catalytic amount of potassium iodide can be added thereto. As a solvent, for example, an alcohol such as methanol, ethanol, or butanol; an aromatic compound such as benzene, toluene, xylene, or pyridine; an ether such as diethylether, tetrahydrofuran, or dioxane; an amide such as dimethylformamide or dimethylacetamide; or a ketone such as dimethylsulfoxide or acetone is used. While the reaction temperature and reaction time may be changed according to the material compounds used, the reaction is usually effected at a temperature within the range of 0° C. to the reflux temperature of the solvent.

Specifically, for example, the compound (IX) is dissolved in tetrahydrofuran or dimethylformamide and, after sodium hydride as a base is added and stirred therein, the halide(X) is added thereto so as to effect a reaction at a temperature within the range of room temperature to the reflux temperature of the solvent, thereby attaining the aimed object.

The hydrolysis at the second step of this reaction can be effected under a reaction condition similar to that of the second step in reaction formula C.

As the reaction formula E shown in FIG. 5, even when a cyano compound (XII) is reacted with a substituted pyridine compound (IX) and the cyano group is reduced, the amine (III) can be synthesized Here, in the reaction formula E, A represents —S— or —NH—, while $R_2$ and $R_3$ are defined as those in formula 1. B represents a halogen atom or hydroxy group.

At the first step of this reaction, when B is a halogen atom, the reaction can be effected under a reaction condition similar to that of the first step in reaction formula D.

When B is hydroxy group, Raney nickel, copper salt, ruthenium, potassium hydroxide, or the like is used as a catalyst. As a solvent, for example, an aromatic compound such as benzene, toluene, xylene, or pyridine; an ether such as diethylether, tetrahydrofuran, or dioxane; or water is used. Also, the compound (XII) itself can be used as a solvent. While the reaction temperature and reaction time may be changed according to the material compounds used, the reaction is usually effected at a temperature within the range of 0° C. to the reflux temperature of the solvent.

Specifically, for example, in the presence of potassium hydroxide, the compound (IX) is reacted with the compound (XII) in water at the reflux temperature of the solvent, thereby attaining the aimed object.

In reduction of the cyano group at the second step in this reaction, a known method can be used. For example, Birch reduction method, a reduction method by metal hydride complex compound, a method using Raney nickel can be used. In Birch reduction, while sodium or lithium is used mainly as a catalyst, the reaction can be effected in the mixed solvent of liquid ammonia and alcohol such as methanol or ethanol. When the metal hydride complex compound is used, as a reagent, lithium aluminum hydride, aluminum hydride, sodium borohydride, or the like can be used. As a solvent, for example, an ether such as diethylether, tetrahydrofuran or dioxane; or an alcohol such as methanol, ethanol, or butanol is used. When sodium borohydride is used, Raney nickel, aluminium chloride, cobalt chloride, or the like can be used as a catalyst. When Raney nickel is used, methanol saturated by ammonia is used as a solvent and hydrogenation is effected under a pressure, thereby attaining the aimed object. While the reaction temperature and reaction time may be changed according to the material compounds used in all cases, the reaction is usually effected at a temperature within the range of 0° C. to the reflux temperature of the solvent.

Specifically, for example, lithium aluminum hydride is suspended in tetrahydrofuran while being cooled with ice and, after the compound (XIII) is dropped thereto, the reaction is effected at a temperature within the range of 0° C. to the reflux temperature of the solvent. Then, the reaction solution is treated with water, aqueous sodium hydroxide solution, or the like, thereby attaining the aimed object.

Figure 6:
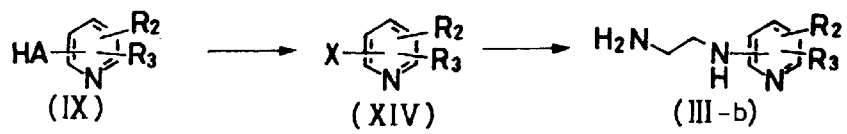
Figure 7:

The compound (III-b) wherein Y is —NH—, p is 1, and m is 2 in the material compound(III) in reaction formula A can be synthesized, for example, by reaction formulas F to G shown in FIGS. 6 to 7.

In reaction formula F shown in FIG. 6, the substituted group of pyridine compound(IX) is converted into halogen atom and then ethylenediamine is reacted thereto so as to synthesize ethylenediamine compound (III-b). Here, in reaction formula F, $R_2$ and $R_3$ are defined as those in formula 1, while X represents a halogen atom. A represents —O— or —NH—.

At the first step of reaction formula F, when A is —O—, as a reagent, for example, phosphorus halogenide, phosphoryl halogenide, or triphenylphosphine halogenide is used. When A is —NH—, a halogenation method by way of diazo compound, for example, such as Sandmeyer reaction or Gattermann reaction can be used. As a catalyst, for example, copper salt, copper powder, copper chloride, copper bromide, copper sulfate, or the like can be used. The reaction can be effected in the presence of sulfuric acid, hydrochloric acid, hydrobromic acid, or the like. Also, diazo process of an amine, for example, can be effected in the presence of hydrochloric acid by using sodium nitrite. As a solvent, for example, an alcohol such as methanol, ethanol, or butanolan; an aromatic compound such as benzene, toluene, xylene, or pyridine; an ether such as diethylether, tetrahydrofuran, or dioxane; a ketone such as dimethylsulfoxide or acetone; acetic acid; phosphoric acid; or water is used. While the reaction temperature and reaction time in any reactions may be changed according to the material compounds used in either case, the reaction is usually effected at a temperature within the range of 0° C. to the reflux temperature of the solvent.

Specifically, for example, in the presence of hydrobromic acid, the compound (IX) is reacted with bromine in water at a temperature within the range of −10° C. to 0° C. Further, the resulting mixture is reacted with sodium nitrite in water at a temperature within the range of 0° C. to the reflux temperature of the solvent, thereby attaining the aimed object.

At the second step of reaction formula F, the reaction can be effected under a reaction condition similar to that of the first step in reaction formula D.

In the reaction formula G of FIG. 7, the ketone group of the amide compound (XV) is reduced so as to synthesize ethylenediamine compound (III-b). Here, in reaction formula G, $R_2$ and $R_3$ are defined as those in formula 1 mentioned above.

In reaction formula G, as a reducing reagent, for example, lithium aluminum hydride, aluminum hydride, or sodium borohydride and triethyloxonium tetrafluoroborate can be used. As a solvent, for example, a halogenated hydrocarbon such as dichloromethane or chloroform; an aromatic compound such as benzene, toluene, xylene, or pyridine; an alcohol such as methanol, ethanol, or butanol; or an ether such as diethylether, tetrahydrofuran or dioxane is used. While the reaction temperature and reaction time in any reactions may be changed according to the material compounds used, the reaction is usually effected at a temperature within the range of 0° C. to the reflux temperature of the solvent.

Figure 8:
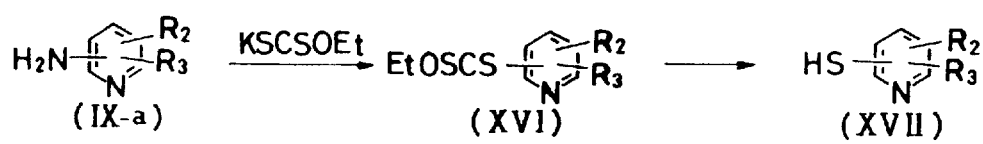

Specifically, for example, lithium aluminum hydride is suspended in tetrahydrofuran while being cooled with ice and, after the compound (XV) is dropped thereto, the reaction is effected at a temperature within the range of 0° C. to the reflux temperature of the solvent. Then, the reaction solution is treated with water, aqueous sodium hydroxide solution, or the like, thereby attaining the aimed object. An aminopyridine (IX-a) is reacted with potassium O-ethyl dithiocarbonate and then hydrolyzed as reaction formula H shown in FIG. 8, the thiol compound (XVII) wherein A is —S— in the material compound(IX) in reaction formulas D to E can be synthesized. In reaction formula H, $R_2$ and $R_3$ are defined as those in formula 1.

The reaction at the first step of this reaction formula H can be effected under the acidic condition and, for example, sodium nitrite is used. Specifically, for example, the compound (IX-a) is dissolved in water under the acidic condition and, after sodium nitrite is added thereto, the reaction is effected at a temperature within the range of 0° C. to room temperature, thereby attaining the aimed object.

Figure 9:
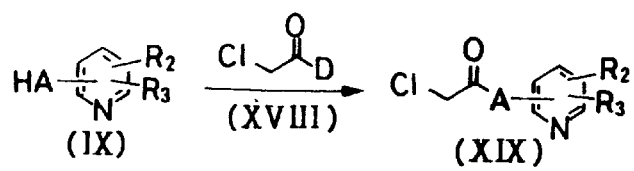

The hydrolysis at the second step of reaction formula H can be effected under a reaction condition similar to that of the second step in reaction formula B. The substituted pyridine compound (IX) is reacted with the compound (XVI) as reaction formula I in FIG. 9, thereby synthesizing the halogenated compound (XIX) wherein Y is —CONH—, p is 1, and m=1 in the material compound (VII) of reaction formula C mentioned above. Here, in reaction formula I, A represents —NH—, while $R_2$ and $R_3$ are defined as those in formula 1. D represents a halogen atom or —OCOCH$_2$ Cl.

In reaction formula I, as an additive, for example, an organic base such as triethyl amine, pyridine, or N-methylmorpholine is used. As a solvent, for example, a halogenated hydrocarbon such as dichloromethane or chloroform; an aromatic hydrocarbon such as benzene, toluene, or xylene; an ether such as tetrahydrofuran or dioxane; or an amide such as dimethylformamide or dimethylacetamide is used. While the reaction temperature and reaction time may be changed according to the material compounds used, the reaction is usually effected at a temperature within the range of 0° C. to the reflux temperature of the solvent.

Specifically, for example, the substituted pyridine compound(IX) and triethylamine are dissolved in benzene and, after the halogenated compound(XVIII) is dropped thereto, the reaction is performed at a temperature within the range of room temperature to the reflux temperature of the solvent, thereby attaining the aimed object.

Figure 10:
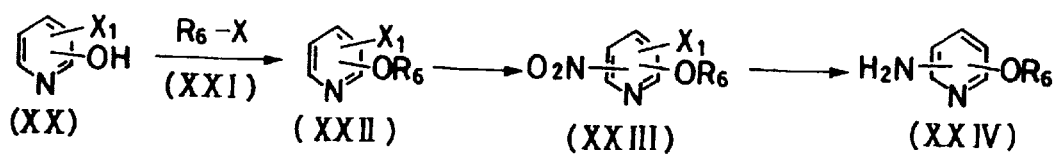

As reaction formula J in FIG. 10, the hydroxypyridine compound (XX) is alkylated and, after a nitro group is introduced thereto, the nitro group is reduced thereby synthesizing the aminopyridine compound substituted by an alkoxy group(XXIV) wherein A is —NH—, $R_2$ is hydrogen atom, and $R_3$ is a lower alkoxy group in the material compound (IX) in reaction formulas D to F and I mentioned above, for example. Here, in reaction formula J, $X_1$ represents a halogen atom or hydrogen atom, while X represents a halogen atom. $R_6$ represents a lower alkyl group.

The alkylation at the first step of this reaction can be effected under a reaction condition similar to that of the first step in reaction formula B.

For the reaction at the second step, for example, a method using a mixed acid of nitric acid and sulfuric acid as a nitrating agent, a synthesizing method using nitronium salt such as nitronium tetrafluoroborate, or dinitrogen pentaoxide can be used. In the case of synthesis by using nitronium tetrafluoroborate, the reaction can be effected in the presence of a Friedel-Crafts type reagent such as boron trifluoride, aluminium chloride, or orthophosphoric acid. When the mixed acid or dinitrogen pentaoxide is used, a halogenated hydrocarbon such as dichloromethane or chloroform, or the like is used as a solvent. While the reaction temperature and reaction time may be changed according to the material compounds used in all cases, the reaction is usually effected at a temperature within the range of −10° C. to the reflux temperature of the solvent.

Specifically, for example, the substituted pyridine compound(XXII) is dissolved in dichloromethane and, after fuming nitric acid and sulfuric acid are added thereto, the reaction is effected at a temperature within the range of 0° C. to the reflux temperature of the solvent, thereby attaining the aimed object.

For the reduction of the nitro group and halogen, at the third step of this reaction a known method can be used. Examples thereof include catalytic hydrogenation and, when $X_1$, is hydrogen atom, Birch reduction and Benkeser reduction. In the case of Birch reduction, for example, the reaction can be effected by using a metal such as lithium, sodium, or potassium and using liquid ammonia as a solvent in the presence of methanol, ethanol, tert-butanol as a proton source. While the reaction temperature and reaction time may be changed according to the material compounds used, the reaction is usually effected at a temperature within the range of −78° C. to the reflux temperature of the solvent. In the case of Benkeser reduction, for example, methylamine, ethylamine, or ethylenediamine is used so as to effect a reaction at a temperature within the range of −78° C. to the reflux temperature of the solvent, thereby attaining the aimed object. When the reaction is effected under the condition of catalytic reduction, as a catalyst, for example, palladium, platinum, nickel, rhodium, ruthenium can be used.

Specifically, for example, the compound (XXIII) is dissolved in ethanol, acetic acid, or tetrahydrofuran and, after palladium-carbon is added thereto, a reaction is effected under a hydrogen gas atmosphere at a temperature within the range of room temperature to the reflux temperature of the solvent, thereby attaining the aimed object.

Figure 11:
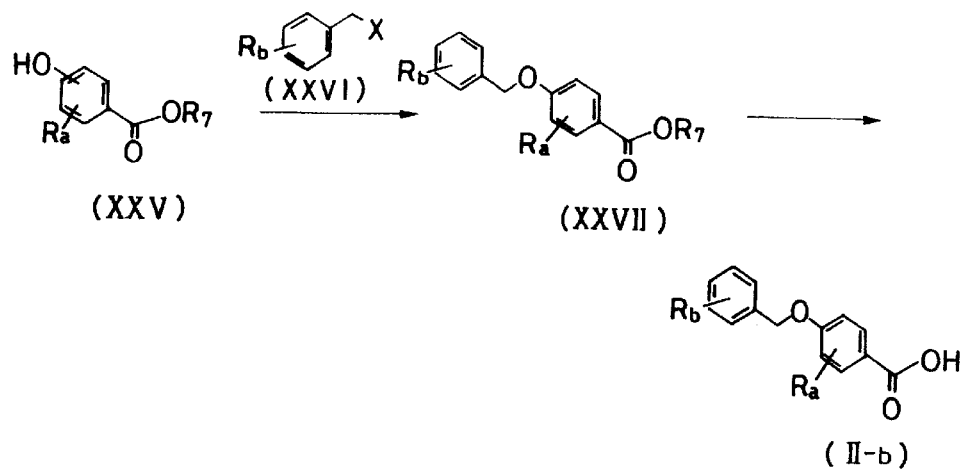

On the other hand, among the carboxylic acid (II) which is a material compound in reaction formula A, the compound (II-b) wherein W is the group expressed by formula 3 above-mentioned can be synthesized according to reaction formula K shown in FIG. 11, for example. In reaction formula K, Ra and Rb are defined as those of formula 3 mentioned above, while X represents a halogen atom. $R_7$ represents a carboxyl-protecting group which may be a lower alkyl group such as methyl group, ethyl group, or tert-butyl group, phenacyl group, or trichloroethyl group as long as no problem occurs in the subsequent reaction.

At the first step of reaction formula K, the compound (XXV) is reacted with the substituted benzyl halide(XXVI) in the presence of a base to obtain the compound (XXVII). As a base in this reaction, for example, an inorganic base such as potassium carbonate, potassium hydroxide, sodium hydroxide, or sodium hydride, or an organic base such as triethylamine or pyridine is used. Specifically, for example, potassium carbonate is used as a base so as to effect a reaction in a solvent such as acetone or N,N-dimethylformamide at a temperature within the range of room temperature to the reflux temperature of the solvent, thereby attaining the aimed object.

At the second step of reaction formula K, the compound (XXVII) is subjected to a deprotecting reaction so as to obtain the carboxylic acid(II-b).

For this deprotecting reaction, various kinds of known methods can be used according to the kind of the protecting group $R_7$. For example, when $R_7$ is methyl or ethyl group, known ester hydrolysis method is used for deprotection. Specifically, for example, an inorganic base such as sodium hydroxide or potassium hydroxide is used so as to effect a reaction in a solvent such as water, methanol, or ethanol at a temperature within the range of room temperature to the reflux temperature of the solvent, thereby attaining the aimed object.

Figure 12:
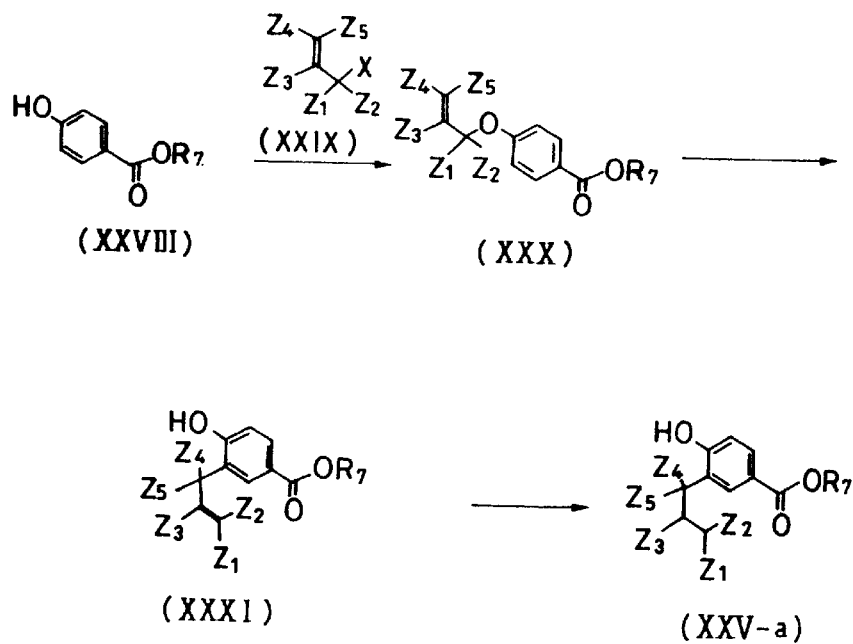

In reaction formula K, the material compound(XXV) may be commercially available or can be synthesized by a known method. For example, the compound (XXV-a) can be manufactured by reaction formula L shown in FIG. 12. In the reaction formula L, each of $Z_1$, $Z_2$, $Z_3$, $Z_4$, and $Z_5$ represents hydrogen atom or a lower alkyl group, while X represents a halogen atom. $R_7$ is defined as that of reaction formula K mentioned above.

At the first step of reaction formula L, the compound (XXVIII) is reacted with the halide (XXIX) in the presence of a base so as to obtain the compound (XXX). As a base in this reaction, for example, an inorganic base such as potassium carbonate, potassium hydroxide, sodium hydroxide, or sodium hydride, or an organic base such as triethylamine or pyridine is used. Specifically, for example, potassium carbonate is used as a base so as to effect a reaction in a solvent such as acetone or N,N-dimethylformamide at a temperature within the range of room temperature to the reflux temperature of the solvent, thereby attaining the aimed object.

At the second step of reaction formula L, the compound (XXX) is subjected to Claisen rearrangement reaction so as to obtain the compound(XXXI). This reaction is effected in or without the presence of a high-boiling solvent under normal or high pressure. Examples of the high-boiling solvent include phenyl ether and N,N-dimethylaniline. While the reaction temperature and reaction time may be changed according to the material compounds used, the reaction is normally effected at a temperature within the range of 100 to 200° C.

At the third step of reaction formula L, the compound (XXV-a) can be obtained by hydrogenation of the compound (XXXI). When this reaction is effected under a catalytic reduction condition, as a catalyst, palladium, platinum, nickel, rhodium, ruthenium, or the like can be used. Specifically, for example, by using palladium-carbon, in a solvent such as ethanol, ethyl acetate, or tetrahydrofuran, under a hydrogen gas atmosphere, a reaction is effected at a temperature within the range of room temperature to the reflux temperature of the solvent, thereby attaining the aimed object.

Among the material compounds used in the above-mentioned reaction formulas, those with no preparation methods described may be commercially available or easily synthesized by using a known method.

Also, examples of salts of the pyridine derivative of the present invention (I) with an acid include salts with inorganic acids such as hydrochloric acid, hydrobromic acid, sulfuric acid, and phosphoric acid and salts with organic acids such as acetic acid, propionic acid, citric acid, lactic acid, oxalic acid, maleic acid, fumaric acid, succinic acid, tartaric acid, and methane sulfonic acid. These salts can be easily manufactured by a normal method.

The pyridine derivative in accordance with the present invention has a strong effect against stress ulcer and an excellent effect for suppressing gastric acid secretion. Further, it has an antibacterial activity against *Helicobacter pyroli* which is supposed to be a cause for recurrence of ulcer. Furthermore, it has a high safety. Accordingly, it is useful as a medicament for curing and preventing peptic ulcer in man or mammals and, particularly, gastric ulcer in man. Conventionally, there has hardly been known such a compound which has both effect for suppressing gastric acid secretion and antibacterial activity against *Helicobacter pyroli*. Accordingly, it is indicated that the compound of the present invention is not only effective in preventing and curing ulcer but also in preventing the recurrence thereof.

When the compound of the present invention is administered as a medicament for curing and preventing peptic ulcer, it may be administered orally as tablet, powder, granule, capsule, syrup, or the like as well as parenterally as suppository, injection, external drug, instillation or the like. While the amount of administration may be outside of the range mentioned below according to the degree of symptom, personal difference, age, kind of ulcer, or the like, it should of course be adjusted so as to fit the individual circumstances in specific cases. Usually 0.01 to 200 mg/kg or, preferably, 0.05 to 50 mg/kg or, more preferably, 0.1 to 10 mg/kg is administered per day for an adult in a single dose or several doses.

When formulating the medicament, a normal manufacturing method is used with a normal formulation carrier. If necessary, pharmacologically and pharmaceutically acceptable additives may be added thereto.

Namely, when preparing an oral solid formulation, after an excipient and, if necessary, a binder, a decaying agent, a luster, a coloring agent, a correctives, and the like are added to the main medicament, a normal method is used to form tablet, coated tablet, granule, powder, capsule, or the like.

Examples of the excipient include lactose, corn starch, sucrose, glucose, sorbitol, crystalline cellulose, and silicon dioxide. Examples of the binder include polyvinylalcohol, polyvinylether, ethyl cellulose, methyl cellulose, gum arabic, tragacanth, gelatin, shellac, hydroxypropyl cellulose, hydroxypropyl starch, and polyvinylpyrrolidone. Examples of the decaying agent include starch, agar, gelatin powder, crystalline cellulose, calcium carbonate, sodium hydrogencarbonate, calcium citrate, dextrin, and pectin. Examples of the luster include magnesium stearate, talc, polyethyleneglycol, silica, and hardened vegetable oil. As the coloring agent, those permitted to be added to medicines are used. Examples of the correctives include cocoa powder, menthol, aromatic acid, mentha oil, borneol, and cinnamon powder. If necessary, these tablet and granule can be coated with sugar-coating, gelatin-coating, and the like.

When preparing an injection, if necessary, a pH-adjusting agent, a buffer, a stabilizer, a solubilizer, and the like are added to the main medicament and then a normal method is used to form subcutaneous, intramuscular, and intravenous injection drugs.

In the following, the present invention will be explained in further detail by specifically examples. However, the present invention should not be restricted to these examples.

First, test methods used for evaluating these examples as an anti-ulcer drug will be explained.

WIS: Restraint and Water Immersion Stress—
Induced Ulcer Inhibition Test i)Meaning The degree of inhibition of the stress ulcer formation is tested.

ii)Method

Male Crj:SD or Slc:SD rats (6 to 7-week-old) were fasted overnight, but allowed free access to water. Each group has 5 to 8 of these rats. The sample compound was dissolved or suspended in an aqueous solution of 0.3% sodium carboxymethylcellulose or 0.05% Tween 80 and then was orally administered (100 mg/10 ml/kg). To a control group, the vehicle was administered. 10 minutes later, the rats were placed in a stress cage and immersed to the level of xipfoid process in a water bath (21° C.) for 7 hours. At the end of the stress, the rats were sacrificed by inhalation of ether or carbon dioxide. Then, the stomach of each was removed, inflated by injecting 10 ml of 5% formalin neutral buffer solution, and immersed in 1% formalin neutral buffer solution for 30 minutes or more to be fixed. The stomach was incised along the greater curvature and then the length of each erosion in the glandular portion was determined under dissecting microscope. The sum of the length of erosions per stomach was defined as ulcer index (UI).

iii)Judgment Standard

The effect obtained when 100 mg/kg of the sample compound had been administered was expressed as ulcer formation inhibitory rate (%) as follows:

ulcer formation inhibitory rate (%)=(1−(UI in sample group/UI in control group))×100

VOL, TAO: Acid Secretion Inhibition Test In Vivo i)Meaning

Inhibitory effect on acid secretion in vivo is confirmed.

ii)Method

Male Crj:Donryu rats (7-week-old) were fasted overnight but allowed free access to water. In each group, 8 to 10 of these rats were used under urethane anesthesia (1.25 g/kg). The sample compound dissolved or suspended in an aqueous solution of 0.5% sodium carboxymethylcellulose or 0.05% Tween 80 was orally administered (100 mg/10 ml/kg). 30 minutes later, the abdomen of each was incised and the pylorus was ligated. 30 minutes after the ligation, 30 mg/kg of histamine dissolved in physiological saline was subcutaneously administered and, 3 hours thereafter, the rat was sacrificed with carbon dioxide. Immediately thereafter, each stomach was removed and the gastric contents were collected and each volume was determined. The total acid output was determined by titration of the gastric juice with 0.1N NaOH.

iii)Judgment Standard

With respect to the gastric juice volume (VOL) and the total acid output (TAO), the effects obtained when 100 mg/kg of the sample compound had been administered were expressed as their respective inhibitory rates (%) as follows:

each inhibitory rate (%)=(1−(value in sample group/value in control group))×100

CAP: Acid Secretion Inhibition Test In Vitro i)Meaning

The acid secretion inhibitory activity in a cell level is studied. It can also be used for studying the mechanism of the effect.

ii)Method ii-a) Preparation of Isolated Gastric Fundus Gland Suspension

First, an isolated gastric fundic gland sample was prepared. Namely, a male Japanese White rabbit (2.5 to 3 kg) was anesthetized to death with Nembutal™ and then the abdomen was incised. Immediately thereafter, the stomach was removed and, after its pyloric and cardiac antrum were severed, incised along its greater curvature into two sheets. The gastric contents adhering to the mucosal surface was washed out with ice-cooled PBS (−) and then carefully washed therein. The gastric wall was spread on a cork board with its mucosal surface facing up and the feed and mucus thereon were completely removed with sterile gauze. The mucosa was separated therefrom by a spatula and then collected in ice-cooled PBS (−). After being washed twice with PBS (−), the mucosa was minced into 2–3 mm³ pieces by scissors. These pieces were further washed twice with a nutrient solution. The nutrient solution comprises 132.4 mM of NaCl, 5.4 mM of KCl, 5 mM of $Na_2HPO_4.12H_2O$, 1 mM of $NaH_2PO_4.2H_2O$, 1.2 mM of $MgSO_4$, 1 mM of $CaCl_2$, 25 mM of HEPES, 2 mg/ml of glucose, and 1 mg/ml of BSA. Into 70 ml of the nutrient solution containing 1 mg/ml of collagenase, minced mucosal pieces were dispersed and intensely stirred in a conical flask with a stirrer at 37° C. for 40 to 60 minutes. During this period, 100% $O_2$ was sprayed on the nutrient solution surface and the pH was appropriately measured such that it was immediately adjusted to pH 7.4, when the value was therebelow, with a base. The nutrient solution was added to the reaction solution so as to attain the total amount of about 200 ml. After being filtered through a mesh, the suspension was divisionally introduced into 50 ml centrifuge tubes and left for 15 minutes such that gastric fundic gland was deposited. The supernatant was repeatedly removed by an aspirator, dispersed in the nutrient solution, and then left such that the gastric fundic gland was washed three times. At this time, without using a pipette, the suspension was alternately introduced into two centrifuge tubes so as to effect dispersion. The number of cells was counted under microscope and adjusted to $1.6 \times 10^6$ cells/ml.

ii-b) [$^{14}$C]-aminopyrine Uptake Test

Then, [$^{14}$C]-aminopyrine uptake test was performed. After an Eppendorf tube was weighed, 10 μl (final concentration: $10^{-5}$M) of histamine dissolved in the above-mentioned nutrient solution, 10 μl (final concentration: $10^{-5}$M) of the test compound dissolved in DMSO, and 10 μl (final concentration: 0.05 μCi/ml) of [$^{14}$C]-aminopyrine diluted with the nutrient solution were introduced therein and then 970 μl of the isolated gastric fundic gland suspension prepared above was added thereto. Subsequently, this mixture was shaken at 37° C. for 40 minutes at 125 cycles/minute. After being centrifuged for 30 minutes, 200 μl of its supernatant was collected into a mini-vial, while the rest was removed by an aspirator. The gland pellet was completely dried as the tube with its lid being opened was kept for one night in a drying oven at 80° C. and then the lid was closed and the weight was determined at room temperature. Then 100 μl of 1N KOH was added thereto and the tube with its lid being closed was treated at 60° C. for 1 to 2 hours so as to dissolve the pellet. Then, the contents thereof were transferred to a mini-vial. Into the mini-vial containing the supernatant or gland pellet, 4 ml of Atomlite™ was added and then the radioactivity was measured by a liquid scintillation counter. Here, after the radioactivity of the gland pellet was corrected by using a sample in which 20 mM of NaSCN was added so as to cancel the hydrogen ion concentration gradient, the integration ratio of aminopyrine specifically trapped by the gland pellet was calculated. This experiment was performed in duplicate.

ii-c) Calculation of the accumulation rate of aminopyrine

Here, its principle will be briefly explained. In the isolated gastric fundic gland, acid is accumulated in a space between its secretory tubule and intraglandular cavity. Aminopyrine is weak base (pKa=5.0) and nonionic in a neutral solution so as to freely pass through the cell membrane, whereas it is ionized in an acidic solution and thus cannot pass through the cell membrane due to its electric charge. Therefore, aminopyrine is accumulated in a closed acidic space within the isolated gastric fttndic gland. In view of this characteristic, the accumulation rate (R) of aminopyrine is calculated by the following equation:

R=((corrected radioactivity of precipitate)/(radioactivity of supernatant))×(200(mg dry weight of gland pellet))

iii) Judgment Standard

The effect of the sample compound at the final concentration of $10^{-5}$ M was expressed by acid secretion inhibitory rate (%) as follows:

acid secretion inhibitory rate (%)=(1−(R in sample group/R in control group))×100

AHP: Antibacterial Activity Test Against *Helicobacter pyroli* i) Meaning

The minimum inhibitory concentration (MIC) against *Helicobacter pyroli* (microaerophilic gram-negative bacterium which is supposed to deeply involve in pathogenesis, relapse, and recrudescence of ulcer, referred to as "HP" in the following) is measured so as to find out compounds which have antimicrobial activity against *Helicobacter pyroli*.

ii) Method

MICs were determined by the agar dilution method. The stock culture (−80° C.) of HP NCTC 11637 was thawed and cultured on tripticase soy agar supplemented with 5% sheep blood at 37° C. in an atmosphere of 5% $O_2$, 10% $CO_2$, and 85% $N_2$. Grown colonies were transferred to the same plate and precultured for 3 days under the same condition. An appropriate amount of the colony grown on the plate by preculturing was suspended in Mueller Hinton broth till turbidness was recognizable by naked eyes, and diluted 100-fold in the same broth; this resulted in a bacterial suspension for inoculation containing about $10^5$ cfu/ml of the bacteria.

A 1,000 μg/ml solution of the sample compound containing DMSO not more than 25% was serieslly diluted 2-fold in sterile purified water. 100 μl volume from each dilution was mixed thoroughly with 900 μl of brucella agar supplemented with 5% horse blood and solidified in a 24 well micro plate, thereby yielding an MIC measurement plate. 10 μl of the bacterial suspension for inoculation (about $10^3$ cfu) was inoculated on this plate and cultured for 7 days under the same condition as that of preculture. Thereafter, it was judged whether there had been bacteria growth or not.

iii) Judgment Standard

The minimum concentration of the sample compound when there were no visible colonies or, if any, 5 or less colonies of HP was defined as MIC (μg/ml).

PD: Gastric Mucosal Integrity Test i) Meaning

There is a possibility that the anti-ulcer mechanism of the compounds which were effective in the experimental ulcer model may be attributed to adaptive cytoprotection, which means exhibiting of apparent anti-ulcer effect due to increase in the amount of endogenous prostaglandins in the gastric mucosa caused by necrotizing agents. In this case, since the sample compound has a necrotizing effect, it is inappropriate as an anti-ulcer medicament.

Therefore, the gastric mucosal potential difference (PD), which reflects the integrity of the gastric mucosa, is measured so as to confirm that the sample compound has no damaging effect on gastric mucosa, which is toxicity at gastric mucosal level.

ii) Method

Male Crj:SD rats (7 to 8-week-old) were fasted overnight, but allowed free access to water, and then, under urethane anesthesia (1.25 g/kg, i.p.), fixed to a cork board on its back. The abdomen of each rat was incised, and a small incision was made in the forestomach. Then, the inside of the stomach was washed with physiological saline heated at 37° C. From the forestomach, along the greater curvature thereof, the stomach was incised without damaging blood vessels. After the height of the cork board was adjusted on a jack, the stomach was mounted on ex vivo chamber. The area of the gastric mucosa exposed to the inside of this chamber was 2.5 cm$^2$. The inside of the chamber was perfused with physiological saline warmed at 37° C. by micro tube pump. By using an agar bridge containing 3M KCl, the potential difference between the chamber and the abdominal cavity was measured by a PD meter. Here, the rectal temperature was measured to control the body temperature during the experiment. After the PD was sufficiently stabilized, the perfusate was stopped and then 100 mg/10 ml/kg of the sample compound dissolved or suspended in an aqueous solution of 0.5% sodium carboxymethyl cellulose or 0.05% Tween 80 was administered into the chamber, while PD was recorded for 60 minutes. To a control, the vehicle was administered.

iii)Judgment Standard

The change in PD during 60 minutes after the administration of 100 mg/kg of the sample compound was collectively studied and, with reference to the positive control, classified into 5 levels as follows:

5: Same as the control with no recognizable damage at all.

4: Though a slight PD-decreasing tendency suggesting a slight possibility of mucosal damage is found, there is no problem.

3: Though a weak decrease in PD and a possibility of a weak mucosal damage is recognized, there is no substantial problem.

2: Medium degree of decrease in PD is found and a mucosal damage is recognized.

1: Heavy degree of decrease in PD is found and a remarkable mucosal damage is recognized.

AT: Single Dose Toxicity Pretest i)Method

Male Slc:ICR mice (5-week-old) were used. Each group has 3 to 5 mice and each mouse was fasted, but allowed free access to water, for 4 to 5 hours from 9 a.m. in the test day. Then, 2,000 mg/10 ml/kg of the sample compound dissolved or suspended in an aqueous solution of 0.5% sodium carboxymethyl cellulose was orally administered thereto. To a control, only the vehicle was administered. The behavior and symptom were observed at each of 15 minutes, 30 minutes, 1 hour, 2 hours, and 3 hours after the administration and then daily till one week thereafter. The body weight was measured before and after the fasting as well as at the same time everyday. The dead animals were immediately subjected to autopsy and their organs were observed microscopically. Also, the living animals were sacrificed with ether or carbon dioxide one week after the administration and then their organs were observed microscopically.

ii)Judgment Standard

The toxicity at the single dose of 2,000 mg/kg of the sample compound was expressed as being classified into 5 levels.

5: Mortality rate is 0%; no toxicity is found at all both in behavior and organs.

4: Mortality rate is 0%; while no toxicity is found in organs, slight toxicity is observed in behavior and body weight increase.

3: While there is a dead animal (though not all the animals are dead), no toxicity is found in organs.

2: Regardless of whether there is a dead animal or not, toxicity is found in organs.

1: All the animals are dead.

MTT: Cell Damaging and Protecting Effect Test i)Meaning

It is confirmed that there is no toxicity in cell level. Those having a toxicity in cell level are inappropriate as an anti-ulcer drug. Also, it can be confirmed that the effects of the sample compounds in other cell level tests do not result from their toxicity.

ii)Method

A male Japanese White rabbit (2.5 to 3 kg) was anesthetized to death by Nembutal™ and, immediately thereafter, its stomach was removed. The greater curvature of the stomach was incised so as to remove the stomach contents therefrom. After the mucosal surface was washed with HBSS (Hanks' Balanced Salt Solution), the stomach in ice-cooled HBSS was transferred to a laboratory. Then, after the pyloric antrum was removed, the gastric corpus mucosa was separated by a spatula and then minced into 2 to 3 mm$^3$ pieces in BME (Basal Medium Eagle). Thereafter, these pieces were shaken at 120 to 130 cycles/minute for 15 minutes at 37° C. in BME 60ml containing 280 U/ml of dispase and 30 to 50 U/ml of collagenase. Here, the concentration of collagenase was appropriately changed for each lot in view of the state of cells. The pieces were washed twice with EBSS (Earle's Balanced Salt Solution) containing 1 mM of EDTA and then shaken in MEM (Minimum Essential Medium) containing 1 mM of EDTA at 37° C. for 5 minutes. Subsequently, they were shaken in the dispase and collagenase having the same concentrations as those mentioned above for 15 minutes so as to remove the supernatant and then further shaken at 37° C. for 50 to 60 minutes at 120 to 130 cycles/minute. Then, after being washed twice with HBSS, Ham F12 containing 2% of Ultrocer GT™ was used to attain the concentration of $1\times10^6$ cells/ml. Thus formed suspension was dispensed in each well of a 96-well plate by 200 μl. The plate was incubated in the atmosphere composed of 5% $CO_2$ and 95% air at 37° C. for three days so as to attain a confluent state and then subjected to MTT assay.

The sample compound was dissolved in DMSO so as to attain a concentration of $10^{-2}$ M and then diluted with HBSS containing 2% of Ultrocer™ so as to attain a final concentration of $10^{-4}$ M. To each group, which 8 wells were used for, 10 μl of MTT reagent was added immediately after 100 μl of the medium in each well was exchanged for same volume of the resulting solution of the sample compound. After being incubated in an atmosphere composed of 5% $CO_2$ and 95% air at 37° C. for 4 hours, thus formed solution was centrifuged and then its supernatant was discarded. Subsequently, 100 μl of 100% ethanol was added to the residue so as to dissolve MTT formazan. Then, the absorbance (OD: 570 to 630) was measured by a microplate reader. This method utilizes a phenomenon in which MTT is changed to MTT formazan only by mitochondria of living cells so as to change color.

iii)Judgment Standard

The cell damaging or cell protecting effect of the sample compound at the final concentration of $10^{-4}$ M was expressed as cell damaging rate (%) as follows:

cell damaging rate (%)=(1−(absorbance in sample group/absorbance in control group))×100

Accordingly, the smaller value is better in the cell damaging rate.

Based on the foregoing effect tests and safety tests, the effect and safety of the example compounds of the present invention were studied.

Compound Group 1

This compound group has a structure expressed by formula 4 mentioned above. As the pyridine derivatives corresponding to this compound group 1, the following compounds were tested. The results of their effect tests and safety tests are shown in Table 1.

Example 1:

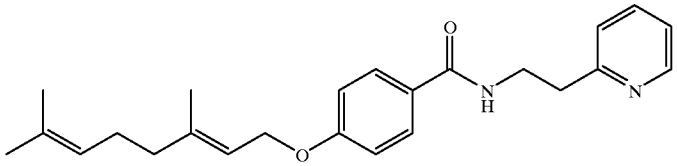

Example 2:

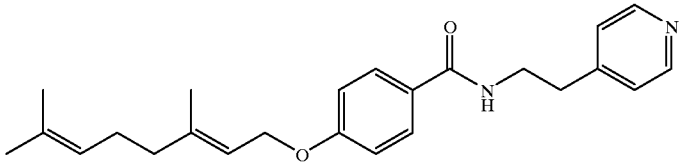

Example 3:

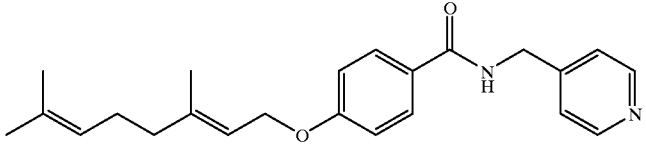

Example 4:

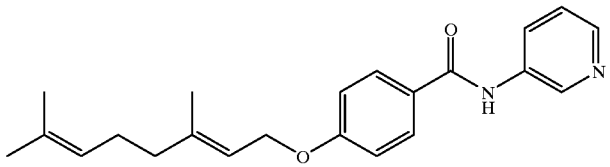

Example 5:

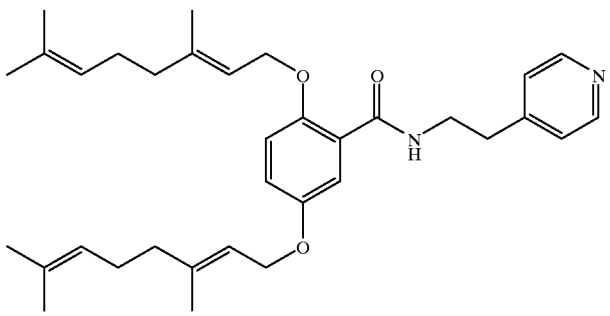

Example 6:

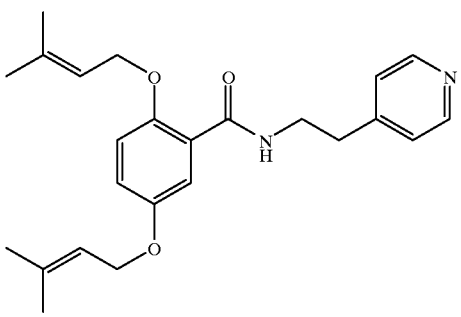

TABLE 1

| Example No. | Anti-ulcer Tests | | | | Tests for Safety | | |
|---|---|---|---|---|---|---|---|
| | WIS | VOL | TAO | CAP | PD | AT | MTT |
| 1 | 50 | 4 | 8 | 97 | 5 | 5 | 8 |
| 2 | 77 | 17 | 25 | 99 | 3 | 5 | 7 |
| 3 | 61 | | | 99 | 3 | 5 | 16 |
| 4 | 39 | | | 44 | 5 | | 6 |
| 5 | 35 | | | 99 | | | -17 |
| 6 | 48 | | | 100 | 5 | | -94 |

As clearly from the Examples 1 to 6 above, it is understood that the compounds expressed by the above-mentioned formula 4 has an excellent anti-ulcer effect and acid secretion inhibition effect. Also, these compounds are excellent in safety.

In this compound group, m is able to change within 0 to 2 and, as to $R_1$, the effects are kept when two lower alkenyloxy groups are introduced on to the aromatic ring as Example 5 or 6.

Compound Group 2

The pyridine derivatives in accordance with this compound group 2 has a structure expressed by formula 5 above-mentioned. As the pyridine derivatives corresponding to the compound group 2, the following Examples 7 to 13 were tested.

The results are shown in Table 2.

TABLE 2

Example 7:

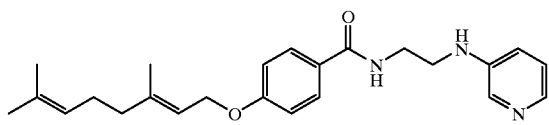

Example 8:

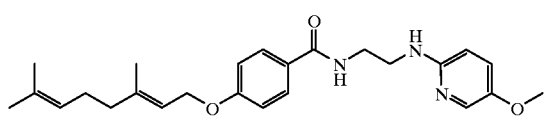

Example 9:

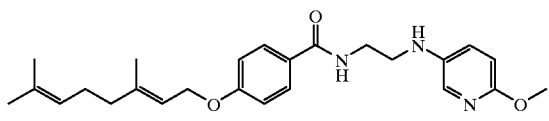

Example 10:

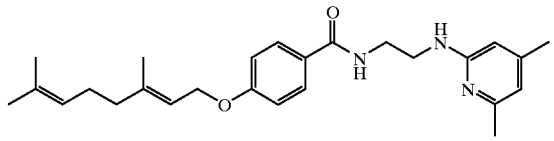

Example 11:

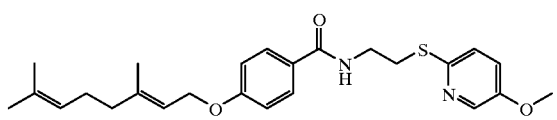

TABLE 2-continued

Example 12:

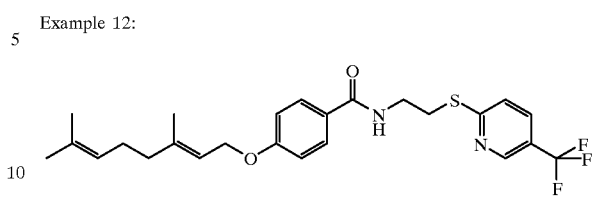

Example 13:

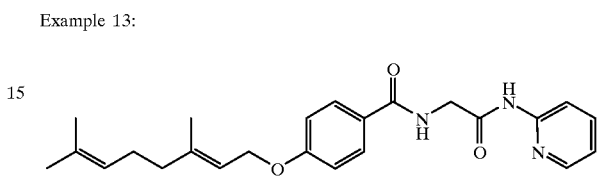

| Example No. | Anti-ulcer Tests | | | | Tests for Safety | | |
|---|---|---|---|---|---|---|---|
| | WIS | VOL | TAO | CAP | PD | AT | MTT |
| 7 | 81 | | | 100 | 3 | | 48 |
| 8 | 55 | 7 | -7 | 97 | 5 | 5 | -45 |
| 9 | 42 | | | 77 | | | 8 |
| 10 | 55 | | | 101 | 3 | 4 | 65 |
| 11 | 61 | | | 55 | 4 | 5 | -34 |
| 12 | 37 | -5 | -10 | | 5 | 5 | -14 |
| 13 | 33 | | | 31 | 5 | 5 | -36 |

As can be seen from the foregoing Examples 7 to 10, when Y is —NH— in this compound group 2, a high anti-ulcer effect, acid secretion inhibition effect, and safety can be obtained. Also, as Examples 11 to 13, sufficient effects were observed in the case where Y is —S— or —CONH—.

In this compound group 2, m, $R_2$, and $R_3$ can be selected with a high degree of freedom, whereby m may be an integer of 0 to 2, while each of $R_2$ and $R_3$ may be hydrogen atom, a lower alkyl group, a lower alkoxy group, or a halogenated alkyl group.

Compound Group 3

The pyridine derivatives in accordance with this compound group 3 has a basic structure expressed by formula 6 mentioned above. As the pyridine derivatives corresponding to this compound group 3, the following Examples 14 to 15 were tested.

TABLE 3

Example 14:

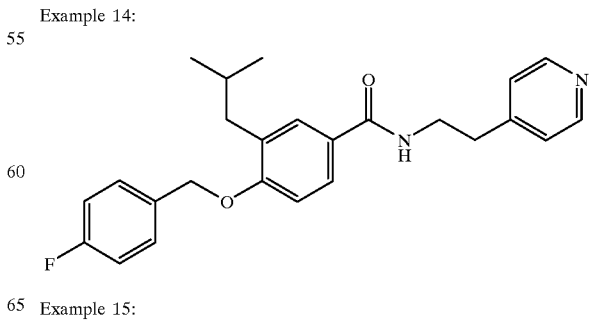

Example 15:

TABLE 3-continued

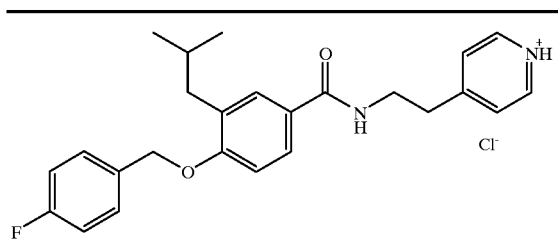

| Example No. | Anti-ulcer Tests | | Anti-HP Test | Tests for Safety |
|---|---|---|---|---|
| | WIS | CAP | AHP | AT |
| 14 | 91 | 97.0 | 6.25~12.5 | 4 |
| 15 | 86 | 95.1 | 6.25~12.5 | |

As can be seen from the foregoing TABLE 3, the compounds of this compound group 3 have antibacterial activity against *Helicobacter pyroli* as well as anti-ulcer effect and acid secretion inhibition effect.

In the following, synthetic methods of intermediates used in Examples explained later will be shown as Reference Examples 1 to 10.

REFERENCE EXAMPLE 1
Synthesis of 4-geranyloxybenzoic Acid

Ethyl 4-hydroxybenzoate (16.6 g), geranyl bromide (23.9 g), and potassium carbonate (27.6 g) were refluxed in acetone (200 ml) with stirring for 1 hour. The reaction mixture, with water added thereto, was extracted with ethyl acetate. The extract was dried over sodium sulfate anhydride. and then concentrated under a vacuum. To the residue dissolved in ethanol (150 ml) were added sodium hydroxide (3.90 g) and water(50 ml) and the mixture was refluxed with stirring for 1 hour. After being concentrated under a vacuum, the reaction mixture was acidified with hydrochloric acid and then extracted with ethyl acetate. The extract was dried over sodium sulfate anhydride and then was concentrated under a vacuum. The resulting solid was recrystallized from n-hexane/ethyl acetate mixed solution, thereby yielding 22.3 g of the aimed compound.

REFERENCE EXAMPLE 2
Synthesis of 2,5-digeranyloxybenzoic Acid 2,5-dihydroxybenzoic acid(11.7 g) and concentrated sulfuric acid(10 ml) were refluxed in ethanol(150 ml) with stirring for 6 hours. After being concentrated under a vacuum, the reaction mixture, with water added thereto, was neutralized with sodium hydrogencarbonate and then extracted with ethyl acetate. The extract was dried over sodium sulfate anhydride and then concentrated under a vacuum. Thus obtained solid dissolved in acetone(150 ml), with geranyl bromide (32.6 g) and potassium carbonate (37.8 g) added thereto, was stirred for 72 hours at room temperature. The reaction mixture, with water added thereto, was extracted with ethyl acetate. The extract was dried over sodium sulfate anhydride and then concentrated under a vacuum. The residue dissolved in ethanol (90 ml), with sodium hydroxide (5.60 g) and water(30 ml) added thereto, was refluxed with stirring for 2 hours. After being concentrated under a vacuum, the reaction mixture was acidified with hydrochloric acid and then extracted with ethyl acetate. The extract was dried over sodium sulfate anhydride and then concentrated under a vacuum, thereby yielding 31.4 g of the aimed compound.

REFERENCE EXAMPLE 3
Synthesis of 2,5-diprenyloxybenzoic acid 2,5-dihydroxybenzoic acid(10.1 g) and concentrated sulfuric acid(10 ml) were refluxed in ethanol(150 ml) with stirring for 23 hours. After being concentrated under a vacuum, the reaction mixture, with water added thereto, was neutralized with sodium hydrogencarbonate and then extracted with ethyl acetate. The extract was dried over sodium sulfate anhydride, and then concentrated under a vacuum. Thus obtained solid dissolved in acetone(40 ml), with prenyl bromide (7.21 g) and potassium carbonate (12.1 g) added thereto, was stirred for 23 hours at room temperature. The reaction mixture, with water added thereto, was extracted with chloroform. The extract was dried over sodium sulfate anhydride and then concentrated under a vacuum. To the residue dissolved in ethanol (70 ml) were added potassium hydroxide (3.08 g) and water(7ml), and the mixture was refluxed with stirring for 5 hours. After being concentrated under a vacuum, the reaction mixture was acidified with hydrochloric acid and then extracted with chloroform. The extract was dried over sodium sulfate anhydride and then concentrated under a vacuum. The residue was purified by silica gel column chromatography (chloroform:acetic acid=60:1), thereby yielding 5.76 g of the aimed compound.

REFERENCE EXAMPLE 4
Synthesis of 3-(2-aminoethylamino)pyridine 3-aminopyridine(1.88 g) and hydroxyacetonitrile(2.49 g) were refluxed in water(20 ml) with stirring for 1.5 hours and then the reaction mixture was extracted with ethyl acetate. The extract was dried over sodium sulfate anhydride and then concentrated under a vacuum. The solution of the residue in tetrahydrofuran(30ml) was dropped into the suspension of lithium aluminium hydride(1.13 g) in tetrahydrofuran (40ml) while being cooled with ice and the mixture was stirred at room temperature for 30 minutes. A small amount of water was added to the reaction mixture and then the resulting deposit was filtrated out. The filtrate was concentrated under a vacuum, thereby yielding 2.24 g of the aimed compound.

REFERENCE EXAMPLE 5
Synthesis of 2-(2-aminoethylamino)-5-methoxypyridine 2-bromo-5-hydroxypyridine(92.5 g), iodomethane(81.2 g), an d potassium carbonate (221 g) were stirred in dimethylformamide (470 ml) for 2 hours at room temperature. The reaction mixture, with water added thereto, was extracted with chloroform. The extract was dried over sodium sulfate anhydride and then concentrated under a vacuum. To the solution of the residue in chlorofom(315 ml) were added fuming nitric acid(315 ml) an d sulfuric acid (157 ml), and then the mixture was stirred at 60° C. for 3 days. The reaction mixture, with water added thereto, was neutralized with sodium hydrogencarbonate and then extracted with chloroform. The extract was dried over sodium sulfate anhydride and then concentrated under a vacuum. The resulting solid was recrystallized from ethanol. To the solution of the crystal in ethanol(10.0L) were added palladium-carbon(10.0 g) and sodium hydroxide(10.3 g) and then the mixture was stirred in hydrogen gas atmosphere at room temperature for 4 hours. After filtration, the filtrate was concentrated under a vacuum. To the residue dissolved in hydrobromic acid (224 ml) was dropped bromine(62.0 g) while being cooled with ice, and the mixture was stirred for 1 hour. After an aqueous solution(58 ml) of sodium nitrous acid(26.6 g) was dropped into the reaction mixture while being cooled with ice, the mixture was stirred for 1.5 hours.

Into the reaction mixture was dropped an aqueous solution (150 ml) of sodium hydroxide(182 g) and then the mixture was stirred for 15 hours at room temperature. After the solution was extracted with isopropylether, the extract was dried over sodium sulfate anhydride and then concentrated under a vacuum. The residue was purified by silica gel column chromatography (n-hexane:ethyl acetate=5:1). The resulting oil dissolved in xylene(150 ml), with ethylenediamine(38.4 g) added thereto, was refluxed with stirring for 24 hours and then concentrated under a vacuum. The residue was purified by silica gel column chromatography (chloroform), thereby yielding 10.9 g of the aimed compound.

REFERENCE EXAMPLE 6

Synthesis of 5-(2-aminoethylamino)-2-methoxypyridine 5-amino-2-methoxypyridine(3.18 g), chloroacetic anhydride(6.56 g), and triethylamine(7.09 ml) were stirred in benzene(55 ml) for 1 hour while being cooled with ice. The reaction mixture, with water added thereto, was extracted with ethyl acetate. The extract was dried over sodium sulfate anhydride and then concentrated under a vacuum. To the solution of the residue in dimethylformamide(20 ml) was added potassium phthalimide(5.21 g) and then the mixture was refluxed with stirring for 3 hours. After a large amount of water was added thereto, the depositing crystal was collected by filtration. The solution of the crystal in ethanol(120 ml), with hydrazine monohydrate(2.56 ml) was refluxed with stirring for 2 hours and then concentrated under a vacuum. The residue, with water added thereto, was acidified with sodium hydrogencarbonate and then extracted with ethyl acetate. The extract was dried over sodium sulfate anhydride and then concentrated under a vacuum. The solution of the residue in tetrahydrofuran(40 ml) was dropped into the suspension of lithium aluminium hydride(2.63 g) in tetrahydrofuran(40 ml) while being cooled with ice and the mixture was stirred at room temperature for 2 hours. A small amount of water was added thereto and the resulting deposit was filtrated out. The filtrate was concentrated under a vacuum, thereby yielding 2.12 g of the aimed compound.

REFERENCE EXAMPLE 7

Synthesis of 2-(2-aminoethylamino)-4,6-dimethylpyridine 2-amino-4,6-dimethylpyridine(1.69 g), chloroacetic anhydride(3.54 g), and triethylamine(3.83 ml) were stirred in benzene(30 ml) for 1 hour while being cooled with ice. The reaction mixture, with water added thereto, was extracted with ethyl acetate. The extract was dried over sodium sulfate anhydride and then concentrated under a vacuum. To the solution of the residue in dimethylformamide(23 ml) was added potassium phthalimide(2.82 g) and then the mixture was refluxed with stirring for 3 hours. After a large amount of water was added thereto, the depositing crystals were collected by filtration. The solution of the crystals in ethanol(50 ml), with hydrazine monohydrate(1.34 ml) added thereto, was refluxed with stirring for 3 hours and then concentrated under a vacuum. The residue, with water added thereto, was acidified with sodium hydrogencarbonate and then extracted with ethyl acetate. The extract was dried over sodium sulfate anhydride and then was concentrated under a vacuum. The solution of the residue in tetrahydrofuran(45ml) was dropped into the suspension of lithium aluminium hydride(0.64 g) in tetrahydrofuran(45 ml) while being cooled with ice and the mixture was stirred at room temperature for 1 hour. A small amount of water was added thereto and then the resulting deposit was filtrated out. The filtrate was concentrated under a vacuum, thereby yielding 1.90 g of the aimed compound.

REFERENCE EXAMPLE 8

Synthesis of 2-(2-aminoethylthio)-5-methoxypyridine 2-bromo-5-hydroxypyridine(42.8 g), iodomethane(37.5 g), and potassium carbonate (102 g) were stirred in dimethylformamide (218 ml) for 2 hours at room temperature. The reaction mixture, with water added thereto, was extracted with chloroform. The extract was dried over sodium sulfate anhydride and then concentrated under a vacuum. To the solution of the residue in chloroform(146 ml) were added fuming nitric acid(146 ml) and sulfuric acid(73 ml), and then the mixture was stirred at 60° C. for 3 days. The reaction mixture, with water added thereto, was neutralized with sodium hydrogencarbonate and then extracted with chloroform. The extract was dried over sodium sulfate anhydride and then concentrated under a vacuum. The resulting solid was recrystallized from ethanol.

To the solution of the crystals in ethanol(4.62 L) were added palladium-carbon(4.62 g) and sodium hydroxide(4.75 g) and then the mixture was stirred in hydrogen gas atmosphere at room temperature for 4 hours. After a filtration, the filtrate was concentrated under a vacuum. To the aqueous solution(13 ml) of the residue were added concentrated hydrochloric acid(25 ml), an aqueous solution(19 ml) of sodium nitrate(7.52 g), an aqueous solution(42 ml) of potassium ethyl-o-dithiocarbonate(20.1 g), and a catalytic amount of nickel chloride while being cooled with ice and the mixture was stirred at 70° C. for 2 hours. The reaction mixture was neutralized with sodium carbonate and then extracted with methylene chloride. The extract was dried over sodium sulfate anhydride and then concentrated under a vacuum. The solution of the residue in ethanol(170 ml), with potassium hydroxide(21.7 g) added thereto, was refluxed with stirring for 3 hours. The insoluble matter was filtrated out and the filtrate was concentrated under a vacuum. The residue, with water added thereto, was extracted with methyl chloride. The extract was dried over sodium sulfate anhydride and then concentrated under a vacuum. To the solution of the residue in dimethylacetamide (150 ml) were added N-(2-bromoethyl)phthalimide(31.8 g), potassium carbonate(11.8 g), and potassium iodide(20.9 g) and the mixture was stirred at 120° C. for 24 hours. The reaction mixture, with water added thereto, was extracted with chloroform. The extract was dried over sodium sulfate anhydride and then concentrated under a vacuum. The residue was purified by silica gel column chromatography (chloroform).

The solution of the resulting oil in methanol(270 ml) and the solution, with hydrazine monohydroxide(4.07 ml) added thereto, was refluxed with stirring for 4 hours and then concentrated under a vacuum. The residue, with water added thereto, was extracted with isopropylether. The extract was dried over sodium sulfate anhydride and then concentrated under a vacuum. The residue was purified by silica gel column chromatography (chloroform: methanol: ammonia-methanol solution=10:1:0.1), thereby yielding 2.03 g of the aimed compound.

REFERENCE EXAMPLE 9

Synthesis of 2-(aminoacethylamino)pyridine 2-aminopyridine(6.00 g) and chloroacetic anhydride(16.4 g) were stirred in benzene(80 ml) at 40° C. for 2 hours. The reaction mixture, with water added thereto, was neutrized with sodium hydrogencarbonate and then extracted with ethyl acetate.

The extract was dried over sodium sulfate anhydride and then concentrated under a vacuum. To the solution of the residue in dimethylformamide(50 ml) was added potassium phthalimide(13.0 g) and then the mixture was refluxed with stirring for 3 hours. After a large amount of water added thereto, the depositing crystals were collected by filtration. The solution of the crystals in ethanol(150 ml), with hydrazine monohydrate(6.19 ml) added thereto, was refluxed with stirring for 2 hours and then concentrated under a vacuum. The residue, with water added thereto, was alkalized with sodium hydroxide and then extracted with ethyl acetate. The extract was dried over sodium sulfate anhydride and then concentrated under a vacuum, thereby yielding 5.31 g of the aimed compound.

REFERENCE EXAMPLE 10

Synthesis of 4-(4-fluorobenzyloxy)-3-isobutylbenzoic Acid

Ethyl 4-hydroxy-3-isobutylbenzoate (25.6 g), potassium carbonate (31.8 g), and 4-fluorobenzyl bromide (26.1 g) were refluxed in acetone (150 ml) with stirring for 4 hours. The reaction mixture, with water added thereto, was extracted with ethyl acetate. The extract was concentrated under a vacuum. The resulting residue, with water (50 ml), potassium hydroxide (12.9 g), and ethanol (100 ml) added thereto, was refluxed with stirring for 2 hours. The reaction mixture, with water added thereto, was neutralized with hydrochloric acid and then extracted with ethyl acetate. The extract was washed with 10% hydrochloric acid and water successively, dried over sodium sulfate anhydride, and then concentrated under a vacuum. Thus obtained solid was recrystallized from n-hexane/ethanol, thereby yielding 30.8 g of the aimed compound.

In the following, the manufacturing method of Examples 1 to 15 which are compounds in accordance with the present invention will be shown.

EXAMPLE 1

2-[2-(4-geranyloxybenzoylamino)ethyl]pyridine 4-geranyloxybenzoic acid(1.37 g) was dissolved in chloroform(30 ml) and triethylamine(1.53 ml), and then diphenylphosphinic chloride(1.05 ml) was added thereto while being cooled with ice. After being stirred for 30 minutes, the mixture, with 2-(2-aminoethyl)pyridine(0.67 g) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol= 40:1). The resulting solid was recrystallized from n-hexane/ ethyl acetate, thereby yielding 1.39 g of the aimed compound.

m.p. 67.0–69.0° C.; $^1$H-NMR (CDCl$_3$) δ: 8.57(1H, s), 7.72(2H, d, J=8.8Hz), 7.64–7.61(1H, m), 7.35(1H, s), 7.26–7.15(2H, m), 6.92(2H, d, J=8.8Hz), 5.47(1H, t, J=6.6Hz), 5.08(1H, t, J=6.6Hz), 4.57(2H,d, J=6.6Hz), 3.86–3.83(2H, m), 3.09(2H, t, J=6.1Hz), 2.12–2.10(4H, m), 1.74(3H, s), 1.67(3H, s), 1.60(3H, s).

EXAMPLE 2

4-[2-(4-geranyloxybenzoylamino)ethyl]pyridine 4-geranyloxybenzoic acid(1.92 g) was dissolved in chloroform(50 ml) and triethylamine(1.96 ml), and then diphenylphosphinic chloride(1.33 ml) was added thereto while being cooled with ice. After being stirred for 30 minutes, the mixture, with 4-(2-aminoethyl)pyridine(0.94 g) added thereto, was stirred for 2 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol= 30:1), thereby yielding 2.26 g of the aimed compound.

m.p. 85.2–86.1° C.; $^1$H-NMR (CDCl$_3$) δ: 8.52(2H, d, J=5.9Hz), 7.66(2H, d, J=8.8Hz), 7.16(2H, d, J=5.9Hz), 6.91(2H, d, J=8.8Hz), 6.19(1H, bs), 5.40–5.48(1H, m), 5.04–5.13(1H, m), 4.57(2H, d, J=6.4Hz), 3.72(2H, q, J=6.8Hz), 2.94(2H, t, J=6.8Hz), 2.03–2.17(1H, m), 1.74(3H, s), 1.67(3H, s), 1.60(3H, s).

EXAMPLE 3

4-(4-geranyloxybenzoylaminomethyl)pyridine 4-geranyloxybenzoic acid(2.47 g) was dissolved in chloroform(50 ml) and triethylamine(2.49 ml), and then diphenylphosphinic chloride(1.72 ml) was added thereto while being cooled with ice. After being stirred for 30 minutes, the mixture, with 4-(aminomethyl)pyridine(0.97 g) added thereto, was stirred for 4 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol= 20:1). The resulting solid was recrystallized from n-hexane/ ethyl acetate, thereby yielding 3.10 g of the aimed compound.

m.p. 108.3–109.5° C.; $^1$H-NMR (CDCl$_3$) δ: 8.51(2H, d, J=5.9Hz), 7.78(2H, d, J=8.8Hz), 7.21(2H, d, J=5.9Hz), 6.92(2H, d, J=8.8Hz), 6.78–7.03(1H, m), 5.47(1H, t, J=6.4Hz), 5.09(1H, t, J=6.4Hz), 4.60(2H, d, J=5.9Hz), 4.58 (2H, d, J=6.4Hz), 1.95–2.26(4H, m), 1.74(3H, s), 1.68(3H, s), 1.60(3H, s).

EXAMPLE 4

3-(4-geranyloxybenzoylamino)pyridine

Sodium hydride(0.74 g) and 3-aminopyridine(0.87 g) were stirred in tetrahydrofuran(30 ml) for 1 hour while being cooled with ice. 4-geranyloxybenzoic acid(2.54 g) and N,N'-carbonyldiimidazole(1.65 g) was stirred in tetrahydrofuran (10 ml) for 30 minutes at room temperature and the mixture was added to the former reaction mixture. After being stirred for 20 minutes at room temperature, the reaction mixture was concentrated under a vacuum. The residue, with water added thereto, was extracted with ethyl acetate. The extract was dried over sodium sulfate anhydride and then concentrated under a vacuum. The residue was purified by silica gel column chromatography (chloroform:methanol=20:1). The resulting solid was recrystallized from n-hexane/ethyl acetate, thereby yielding 1.05 g of the aimed compound.

m.p. 101.8–102.8° C.; $^1$H-NMR (CDCl$_3$) δ: 8.65(1H, d, J=2.5Hz), 8.35(1H, dd, J=1.5, 4.4Hz), 8.29(1H ddd, J=1.5, 2.5, 8.3Hz), 8.08(1H, s), 7.85(2H, d, J=8.8Hz), 7.30(1H, dd, J=4.4, 8.3Hz), 6.97(2H, d, J=8.8Hz), 5.48(1H, t, J=6.4Hz), 5.09(1H, t, J=5.9Hz), 4.60(2H, d, J=6.4Hz), 2.01–2.25(4H, m), 1.76(3H, s), 1.68(3H, s), 1.61(3H, s).

EXAMPLE 5

4-[2-(2,5-digeranyloxybenzoylamino)ethyl/lpyridine 2,5-digeranyloxybenzoic acid(2.40 g) was dissolved in chloroform(40 ml) and triethylamine(1.58 ml), and then diphenylphosphinic chloride(1.08 ml) was added thereto while being cooled with ice. After being stirred for 30 minutes, the mixture, with 4-(2-aminoethyl)pyridine(0.69 g) added thereto, was stirred for 1 hour at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol= 50:1). The resulting solid was recrystallized from n-hexane/ ethyl acetate, thereby yielding 1.90 g of the aimed compound.

m.p. 59.1–60.6° C. $^1$H-NMR (CDCl$_3$) δ: 8.52(2H, dd, J=1.5, 4.4Hz), 8.24–8.34(1H, m), 7.79(1H, d, J=3.4Hz), 7.16(2H, dd, J=1.5, 4.4Hz), 6.99(1H, dd, J=3.4, 8.8Hz), 6.88(1H, d, J=8.8Hz), 5.43–5.53(1H, m), 5.25–5.35 (1H, m), 5.02–5.14(2H, m), 4.55(2H, d, J=6.8Hz), 4.52(2H, d, J=6.4Hz), 3.73 (2H, q, J=6.8Hz), 2.92(2H, t, J=6.8Hz), 1.99–2.17(8H, m), 1.74(3H, s), 1.68(9H, s), 1.60(6H, s).

EXAMPLE 6

4-[2-(2,5-diprenyloxybenzoylamino)ethyl]pyridine 2,5-diprenyloxybenzoic acid(1.99 g) was dissolved in chloroform(38 ml) and triethylamine(1.91ml), and then diphenylphosphinic chloride(1.31 ml) was added thereto while being cooled with ice. After being stirred for 30 minutes, the mixture, with 4-(2-aminoethyl)pyridine(0.85 g) added thereto, was stirred for 1 hour at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol= 50:1). The resulting solid was recrystallized from n-hexane/ ethyl acetate, thereby yielding 2.41 g of the aimed compound.

m.p. 92.7–93.5° C.; $^1$H-NMR (CDCl$_3$) δ: 8.53(2H, d, J=4.4Hz), 8.23–8.32(1H, m), 7.79(1H, d, J=3.4Hz), 7.17 (2H, d, J=4.4Hz), 6.99(1H, dd, J=3.4, 9.3Hz), 6.87(1H, d, J=9.3Hz), 5.44–5.54(1H, m), 5.20–5.30 (1H, m), 4.53(2H, d, J=6.8Hz), 4.49(2H, d, J=6.8Hz), 3.74(2H, q, J=6.8Hz), 2.92(2H, t, J=6.8Hz), 1.79(3H, s), 1.76(3H, s), 1.7(3H, s,), 1.68(3H, s,).

EXAMPLE 7

3-[2-(4-geranyloxybenzoylamino)ethylamino]pyridine 4-geranyloxybenzoic acid(3.57 g) was dissolved in chloroform(60 ml) and triethylamine(3.60 ml), and then diphenylphosphinic chloride(2.48 ml) was added thereto while being cooled with ice. After being stirred for 30 minutes, the mixture, with 3-(2-aminoethylamino)pyridine (2.24 g) added thereto, was stirred for 3 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=15:1). The resulting solid was recrystallized from n-hexane/ethyl acetate, thereby yielding 2.41 g of the aimed compound.

m.p. 88.5–89.2° C.; $^1$H-NMR (CDCl$_3$) δ: 8.02(1H, s), 7.94(1H, d, J=4.4Hz), 7.73(2H, d, J=8.3Hz), 7.07(1H, dd, J=4.4, 8.3Hz), 6.79–7.04(3H, m), 6.62(1H, bt), 5.47(1H, t, J=6.4Hz), 5.08(1H, t, J=6.4Hz), 4.57(2H, d, J=6.4Hz), 4.03–4.78(1H, bs), 3.70(2H, q, J=5.9Hz), 3.37(2H, t, J=5.9Hz), 1.95–2.27(4H, m), 1.74(3H, s), 1.67(3H, s), 1.60 (3H, s).

EXAMPLE 8

2-[2-(4-geranyloxybenzoylamino)ethylamino]-5-methoxypyridine 4-geranyloxybenzoic acid(1.92 g) was dissolved in chloroform(50 ml) and triethylamnine(1.95 ml), and then diphenylphosphinic chloride(1.34ml) was added thereto while being cooled with ice. After being stirred for 1 hour, the mixture, with 2-(2-aminoethylamino)-5-methoxypyridine(1.17 g) added thereto, was stirred for 8 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=20:1). The resulting solid was recrystallized from n-hexane/ethyl acetate, thereby yielding 2.22 g of the aimed compound.

m.p. 70.8–71.7° C.; $^1$H-NMR (CDCl$_3$) δ: 7.80(1H, d, J=2.9Hz), 7.75(1H, m), 7.73(2H, d, J=8.8Hz 7.09(1H, dd, J=2.9, 9.3Hz), 6.90(2H, d, J=8.8Hz), 6.43(1H, d, J=9.3Hz), 5.47(1H, t, J=6.4Hz), 5.09(1H, t, J=6.8Hz), 4.57–4.83(1H, bs), 4.57(2H, d, J=6.4Hz), 3.78(3H, s), 3.47–3.72(4H, m), 2.03–2.19(4H, m), 1.74(3H, s), 1.68(3H, s), 1.60(3H, s).

EXAMPLE 9

3-[2-(4-geranyloxybenzoylamino)ethylamino]-6-methoxypyridine 4-geranyloxybenzoic acid(3.48 g) was dissolved in chloroform(50 ml) and triethylamine(3.52 ml), and then diphenylphosphinic chloride(2.42 ml) was added thereto while being cooled with ice. After being stirred for 1 hour, the mixture, with 3-(2-aminoethylamino)-6-methoxypyridine(2.12 g) added thereto, was stirred for 3 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=20:1). The resulting solid was recrystallized from n-hexan/ethyl acetate, thereby yielding 1.39 g of the aimed compound.

m.p. 97.9–99.3° C.; $^1$H-(CDCl$_3$) δ: 7.71(2H, d, J=8.8Hz), 7.59(1H, d, J=2.9Hz), 7.01(1H, dd, J=2.9, 8.8Hz), 6.91(2H, d, J=8.8Hz), 6.61(1H, d, J=8.8Hz), 6.46(1H, t, J=5.9Hz), 5.47(1H, t, J=6.4Hz), 5.07(1H , t, J=6.8Hz), 4.57(2H, d, J=6.4Hz), 3.86(3H, s), 3.69(2H, q, J=5.9Hz), 3.33(2H, t, J=5.9Hz), 2.02–2.20(4H, m), 1.74(3H, s), 1.67(3H, s), 1.60 (3H, s).

EXAMPLE 10

2,4-dimethyl-6-[2-(4-geranyloxybenzoylamino) ethylamino]pyridine 4-geranyloxybenzoic acid(2.30 g) was dissolved in chloroform(50 ml) and triethylamine(2.33 ml), and then diphenylphosphinic chloride(1.48 ml) was added thereto while being cooled with ice. After being stirred for 45 minutes, the mixture, with 2-(2-aminoethylamino)-4,6-dimethylpyridine(1.90 g) added thereto, was stirred for 3 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=20:1). The resulting solid was recrystallized from n-hexane/ethyl acetate, thereby yielding 2.79 g of the aimed compound.

$^1$H-NMR (CDCl$_3$) δ: 7.97(1H, bs), 7.69(2H, d, J=8.8Hz), 6.84(2H, d, J=8.8Hz), 6.27(1H, s), 6.06(1H, s), 5.46(1H, t, J=6.4Hz), 5.16–5.42(1H, bs), 5.08(1H, t, J=6.4Hz), 4.53(2H, d, J=6.4Hz), 3.38–3.78(4H, m), 2.32(3H, s), 2.13(3H, s), 1.98–2.27(4H, m), 1.73(3H, s), 1.67(3H, s), 1.60(3H, s).

EXAMPLE 11

2-[2-(4-geranyloxybenzoylamino)ethylthio]-5-methoxypyridine 4-geranyloxybenzoic acid(1.92 g) was dissolved in chloroform(40 ml) and triethylamine(1.95 ml), and then diphenylphosphinic chloride(1.34 ml) was added thereto while being cooled with ice. After being stirred for 1 hour, the mixture, with 2-(2-aminoethylthio)-5-methoxypyridine (1.29 g) added thereto, was stirred for 17 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=20:1). The resulting solid was recrystallized from n-hexane/ethyl acetate, thereby yielding 2.84 g of the aimed compound.

m.p. 82.6–83.4° C.; $^1$H-NMR (CDCl$_3$) δ: 7.79(1H, d, J=2.9Hz), 7.74(2H, d, J=8.8Hz), 7.23(1H, dd, J=2.9, 8.8Hz), 7.04(1H, m), 6.92(2H, d, J=8.8Hz), 6.72(1H, d, J=8.8Hz), 5.47(1H, t, J=6.4Hz), 5.08(1H, t, J=6.4Hz), 4.57(2H, d, J=6.4Hz), 4.47(2H, t, J=4.9hz), 3.82(2H, q, J=4.9Hz), 3.82 (3H, s), 2.04–2.20(4H, m), 1.74(3H, s), 1.67(3H, s), 1.60 (3H, s).

EXAMPLE 12

2-[2-(4-geranyloxybenzoylamino)ethylthio]-5-trifluoromethylpyridine 4-geranyloxybenzoic acid(6.17 g) was dissolved in chloroform(80 ml) and triethylamine(6.24 ml), and then diphenylphosphinic chloride(4.29 ml) was added thereto while being cooled with ice. After being stirred for 1 hour, the mixture, with 2-(2-aminoethylthio)-5-(trifluoromethyl) pyridine(5.00 g) added thereto, was stirred for 4 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=20:1). The resulting solid was recrystallized from n-hexane/ethyl acetate, thereby yielding 9.02 g of the aimed compound.

m.p. 96.7–97.5° C.; $^1$H-NMR (CDCl$_1$) δ: 8.66(1H, s), 7.69(1H, d, J=8.3Hz), 7.66(2H, d, J=8.8Hz), 7.35(1H, d, J=8.3Hz), 7.04(1H, t, J=5.9Hz), 6.89(2H, d, J=8.8Hz), 5.47 (1H, t, J=6.8Hz), 5.09(1H, t, J=6.6Hz), 4.57(2H, d, J=6.8Hz), 3.80(2H, q, J=5.9Hz), 3.49(2H, t, J=5.9Hz), 2.03–2.20(4H, m), 1.74(3H, s), 1.68(3H, s), 1.60(3H, s).

EXAMPLE 13

2-[2-(4-geranyloxybenzoylamino)acetylamino]pyridine 4-geranyloxybenzoic acid(1.81 g) was dissolved in chloroform(40 ml) and triethylamine(1.84 ml), and then diphenylphosphinic chloride(1.26 ml) was added thereto while being cooled with ice. After being stirred for 30 minutes, the mixture, with 2-(aminoacetylamino)pyridine (1.00 g) added thereto, was stirred for 2 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=20:1). The resulting solid was recrystallized from n-hexane/ethyl acetate, thereby yielding 1.84 g of the aimed compound.

m.p. 105.2–106.2° C.; $^1$H-NMR (CDCl$_3$) δ: 9.01(1H, s), 8.30(1H, d, J=4.9Hz), 8.18(1H, d, J=7.8Hz), 7.84(2H, d, J=8.8Hz), 7.72(1H, dd, J=7.4, 7.8Hz), 7.06(1H, dd, J=4.9, 7.4Hz), 7.02–7.15(1H, m), 6.94(2H, d, J=8.8Hz), 5.48(1H, t, J=6.8Hz), 5.09(1H, t, J=6.3Hz), 4.58(2H, d, J=6.8Hz), 4.36 (2H, d, J=4.9Hz), 2.02–2.24(4H, m), 1.75(3H, s), 1.68(3H, s), 1.61(3H, s).

EXAMPLE 14

4-[2-[4-(4-fluorobenzyloxy)-3-isobutylbenzoylamino]ethyl]pyridine 4-(4-fluorobenzyloxy)-3-isobutylbenzoic acid(1.51 g) was dissolved in chloroform(50 ml) and triethylamine(1.38 ml), and then diphenylphosphinic chloride(0.95 ml) was added thereto while being cooled with ice. After being stirred for 30 minutes, the mixture, with 4-(2-aminoethyl) pyridine(0.61 g) added thereto, was stirred for 2 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=20:1). The resulting solid was recrystallized from n-hexane/ethyl acetate, thereby yielding 1.74 g of the aimed compound as white crystals.

m.p. 111.8–112.3° C.; $^1$H-NMR (CDCl$_3$) δ: 8,51(2H, d, J=5.9Hz), 7.54–7.50(2H, m), 7.38(2H, dd, J=5.4, 8.3Hz), 7.16(2H, d, J=5.4Hz), 7.08(2H, t, J=8.3Hz), 6.87(2H, d, J=8.3Hz), 6.23(1h, t, J=5.4Hz), 5.06(2H, s), 3.71(2H, q, J=6.8Hz), 2.94(2H, t, J=6.8Hz), 2.53(2H, d, J=6.8Hz), 1.98–1.82(1H, m), 0.87(6H, d, J=6.4Hz).

EXAMPLE 15

4-[2-[4-(4-fluorobenzyloxy)-3-isobutylbenzoylamino]ethyl]pyridine hydrochloride

The compound obtained in Example 14(1.49 g) was dissolved in a mixed solvent of diethylether(40 ml) and tetrahydrofuran(5 ml), and then 1N hydrochloric acid ether solution(10 ml) was added thereto. After being stirred for 5 minutes at room temperature, the depositing crystals were collected by filtration, thereby yielding 1.54 g of the aimed compound as white crystals.

m.p. 166.2–169.5° C.; $^1$H-NMR (CDCl$_3$) δ: 8,51(2H, d, J=5.4Hz), 7.83(2H, d, J=5.4Hz), 7.73(1H, d, J=8.3Hz), 7.69–7.62(2H, m), 7.38–7.34(2H, m), 7.05(2H, t, J=8.8Hz), 6.85(1H, d, J=8.8Hz), 5.03(2H, s), 3.81(2H, q, J=5.4Hz), 3.27(2H, t, J=5.9Hz), 2.50(2H, d, J=7.3Hz), 1.98–1.82(1H, m), 0.85(6H, d, J=6.8Hz).

What is claimed is:

1. A pyridine derivative or a pharmacologically acceptable salt thereof expressed by the following formula 1:

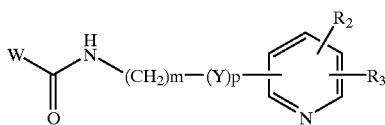

formula 1 wherein W represents a group expressed by the following formula 2 or formula 3:

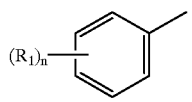

formula 2

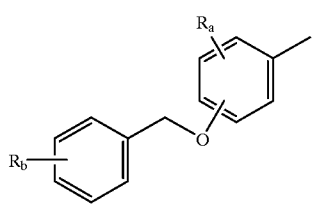

formula 3 wherein $R_1$ represents an alkenyloxy group; n represents 1 or 2; each of $R_2$ and $R_3$ represents a hydrogen atom, a lower alkyl group, a lower alkoxy group, or a halogenated alkyl group; Ra represents a lower alkyl; and Rb represents a halogen atom; Y represents a group expressed by —NH— or —CONH—; m represents an integer of 0 to 2, wherein when Y is —NH—, m is 1 or 2; and p represents 1.

2. A pyridine derivative or a pharmacologically acceptable salt thereof according to claim 1, wherein n is 1 and $R_1$ is bonded to para-position of an amide group.

3. A pyridine derivative or a pharmacologically acceptable salt thereof according to claim 1, wherein n is 2.

4. A pyridine derivative or a pharmacologically acceptable salt thereof according to claim 1, which expressed by the following formula 5.

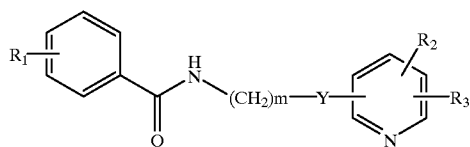

formula 5 wherein $R_1$, $R_2$, $R_3$, Y, and m are same as those in the above-mentioned formula 1.

5. A pyridine derivative or a pharmacologically acceptable salt thereof according to claim 4, wherein Y is a group expressed by —NH—.

6. A pyridine derivative or a pharmacologically acceptable salt thereof according to claim 4, wherein $R_1$ is bonded to para-position.

7. A pyridine derivative or a pharmacologically acceptable salt thereof according to claim 1, wherein $R_1$ is prenyloxy group or geranyloxy group.

8. An anti-ulcer composition comprising, as an effective ingredient, a pyridine derivative or a pharmacologically acceptable salt thereof according to claim 1, together with a pharmaceutically acceptable carrier and/or adjuvant.

9. An antibacterial composition for inhibiting the growth of *Helicobacter pyroli* comprising, as an effective ingredient, a pyridine derivative or a pharmacologically acceptable salt thereof according to claim 1, together with a pharmaceutically acceptable carrier and/or adjuvant.

10. A method for the treatment of peptic ulcers in man or mammals in need of said treatment, which comprises administering an effective amount of a pyridine derivative or a pharmacologically acceptable salt thereof according to claim 1 to a host.

11. A method according to claim 10, wherein said peptic ulcers are gastric ulcers in man.

12. A method for the inhibition of acid secretion in stomach of man or mammals, which comprises administering an effective amount of a pyridine derivative or a pharmacologically acceptable salt thereof according to claim 1 to a host.

13. A method for the inhibition of growth of *Helicobacter pyroli* in stomach of man or mammals, which comprises administering an effective amount of a pyridine derivative or a pharmacologically acceptable salt thereof according to claim 1 to a host.

14. A method for treating of peptic ulcers in man or mammals in need of said treatment, which comprises administering an effective amount of a pyridine derivative or a pharmacologically acceptable salt thereof according to claim 1 to a host.

15. A method according to claim 14, wherein said peptic ulcers are gastric ulcers in man.

16. A pyridine derivative and a pharmacologically acceptable salt thereof according to claim 1, wherein said alkenyloxy group of $R_1$ comprises a straight or branched alkenyl group having at least one double bond with 2 to 20 carbon atoms.

17. A pyridine derivative and a pharmacologically acceptable salt thereof according to claim 16, wherein said alkenyloxy group of $R_1$ is selected from the group consisting of geranyloxy, prenyloxy, neryloxy, and farnesyloxy.

* * * * *